(12) United States Patent
Lu et al.

(10) Patent No.: US 9,289,504 B2
(45) Date of Patent: Mar. 22, 2016

(54) SINGLE PROTEIN NANOCAPSULES FOR PROTEIN DELIVERY WITH LONG-TERM EFFECT

(75) Inventors: Yunfeng Lu, Culver City, CA (US); Ming Yan, Los Angeles, CA (US); Juanjuan Du, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 537 days.

(21) Appl. No.: 13/255,229

(22) PCT Filed: Mar. 9, 2010

(86) PCT No.: PCT/US2010/026678
§ 371 (c)(1),
(2), (4) Date: Sep. 7, 2011

(87) PCT Pub. No.: WO2010/104865
PCT Pub. Date: Sep. 16, 2010

(65) Prior Publication Data
US 2011/0318297 A1    Dec. 29, 2011

Related U.S. Application Data

(60) Provisional application No. 61/158,588, filed on Mar. 9, 2009, provisional application No. 61/254,121, filed on Oct. 22, 2009.

(51) Int. Cl.
*A61K 31/74* (2006.01)
*A61K 47/48* (2006.01)
*A61K 9/51* (2006.01)
*A61K 9/00* (2006.01)

(52) U.S. Cl.
CPC ......... *A61K 47/48176* (2013.01); *A61K 9/5169* (2013.01); *A61K 9/0019* (2013.01)

(58) Field of Classification Search
CPC ........... A61K 9/0019; A61K 47/48176; A61K 9/5169
See application file for complete search history.

(56) References Cited

U.S. PATENT DOCUMENTS

| 6,716,450 | B1 | 4/2004 | Yin et al. | |
|---|---|---|---|---|
| 7,056,901 | B2 | 6/2006 | Frechet et al. | |
| 7,217,410 | B2 | 5/2007 | Suslick et al. | |
| 2005/0008572 | A1 | 1/2005 | Prokop et al. | |
| 2007/0009441 | A1* | 1/2007 | Erathodiyil et al. | 424/9.34 |
| 2008/0248126 | A1* | 10/2008 | Cheng et al. | 424/497 |

FOREIGN PATENT DOCUMENTS

| JP | 02-099522 | 4/1990 |
|---|---|---|
| WO | 2008/109483 | 9/2008 |

OTHER PUBLICATIONS

Lowe et al ("Calcitonin and Insulin in Isobutylcyanoacrylate—Nanocapsules: Protection Against Proteases and—Effect on Intestinal Absorption in Rats," J. Pharm. Pharmacol. 1994,46: 547-552).*
Yan et al ("Encapsulation of Single Enzyme in Nanogel with Enhanced Biocatalytic Activity and Stability," J. Am. Chem. Soc. 2006, 128, 11008-11009).*
Ge, J., et al., Molecular Fundamentals of Enzyme Nanogels, J Phys. Chem. B 2008, 112, pp. 14319-14324.
Yan, M., et al., A novel intracellular protein delivery platform based on single-protein nanocapsules, Nature Nanotechnology, 5, 48-53 (Nov. 22, 2009).
Yan, M., et al., Encapsulation of Single Enzyme in Nanogel with Enhanced Biocatalytic Activity and Stability, J. Am. Chem. Soc. 2006, 128, pp. 11008-11009.
Yan, M., et al., Fabrication of Single Carbonic Anhydrase Nanogel against Denaturation and Aggregation at High Temperature, Biomacromolecules 2007, 8, pp. 560-565.
PCT International Search Report and Written Opinion dated Sep. 30, 2010 (PCT International Application No. PCT/US2010/026678).
Biswas, A. et al., "Endoprotease-Mediated Intracellular Protein Delivery Using Nanocapsules," ACS Nano, 5 (1385) 2011.
Gu, Z. et al., "Tailoring Nanocarriers for Intracellular Protein Delivery," Chemical Society Reviews, in press, 2011.
Gu, Z. et al., "Detection of Mercury Ion by Infrared Fluorescent Protein and Its Hydrogel-Based Paper Assay," Analytical Chemistry, 83(2324), 2011.
Gu, Z. et al., "Probing Protease Activity by Single-Fluorescent-Proteing Nanocapsules," Chemical Communications, 46 (6467), 2010.
Gu, Z. et al., "Enzyme-Assisted Photolithography for Spatial Functionalization of Hydrogels," Lab on a Chip, 10 (1946), 2010.
Gu, Z. et al., "Hybrid Nanocomposites of Semiconductor Nanoparticles and Conjugated Polyelectrolytes and Their Application as Fluorescence Biosensors," Polymer, 51 (902), 2010.
Gu, Z. et al., "Protein Nanocapsule Weaved with Enyzmatically Degradable Polymeric Network," Nano Letters, 12 (4533), 2009.
Gu, Z. et al., "Biomolecular Nanopatterning by Magnetic Electric Lithography," Angewandte Chemie International Edition, 48(952), 2009.
Gu, Z. et al., "Dual Electroluminescence from a Single-Component Light-emitting Electrochemical Cell Based on Water-Soluble Conjugated Polymer," Journal of Applied Polymer Science, 100 (2930), 2006.
Joo, K-Il et al., "Enhanced Real-Time Monitoring of Adeno-Associated Virus Trafficking by Virus-Quantum Dot Conjugates," ACS Nano, in press, 2011.
Lai, Q. et al., An Organic/Si Nanowire Hybrid Field Configurable Transistor, Nano Letters, 3 (876), 2008.
Sun, B. et al., "Conjugated Polymer Fluorescence Probe for Intracellular Imaging of Magnetic Nanoparticles," Macromolecules, 43 (10348), 2010.
Yan, M. et al., "A Novel Intracellular Protein Delivery Platform Based on Single-Protein Nanocapsules," Nature Nanotechnology, 5(48), 2010.

(Continued)

*Primary Examiner* — Suzanne Ziska
(74) *Attorney, Agent, or Firm* — Gates & Cooper LLP

(57) ABSTRACT

A protein nanocapsule having a single-protein core and a thin polymer shell anchored covalently to the protein core.

14 Claims, 27 Drawing Sheets

(56) References Cited

OTHER PUBLICATIONS

Zhao, M. et al., "Redox-Responsive Nanocapsules for Intracellular Protein Delivery," Biomaterials, in press, 2011.
Singapore Written Opinion dated Jan. 17, 2013, Singapore Appln. No. 201106455-7.
Japanese Office Action dated Feb. 26, 2014 for JP application No. 2011554125.
Ichikawa et al., "Design of Nanohydrogel-Incorporated Microcapsules for Appropriate Controlled-Release of Peptide Drugs". The Pharmaccutial Society of Japan, 127(5), 2007, pp. 813-823.
Yan et al , "Encapsulation of Single Enzyme in Nanogel with Enhanced Biocatalytic Activity and Stability". J. Am. Chem. Soc. 128, 2006, pp. 11008-11009.

\* cited by examiner

SINGLE PROTEIN NANOCAPSULES FOR PROTEIN DELIVERY WITH LONG-TERM EFFECT

CROSS-REFERENCE OF RELATED APPLICATION

This application claims priority to U.S. Provisional Application No. 61/158,588, filed Mar. 9, 2009, the entire contents of which are hereby incorporated by reference and U.S. Provisional Application No. 61/254,121, filed Oct. 22, 2009, the entire contents of which are hereby incorporated by reference.

This invention was made with government support under HDTRA1-09-1-0001 awarded by the United States Department of Defense, Defense Threat Reduction Agency. The government has certain rights in the invention.

BACKGROUND

1. Field of Invention

The invention deals with intracellular protein delivery vehicles, methods of preparing them, and their use to deliver proteins to a cellular target.

2. Discussion of Related Art

An average eukaryotic cell contains thousands of different proteins that participate in normal cellular functions. Most human diseases are somehow related to malfunctioning of particular proteins systematically or locally. In this context, protein therapy (Birch et al., *Therapeutic Proteins, methods and Protocols*, (Humana Press, Totowa), pp. 1-16 2005) offers the most direct and safe approach for the treatment of such diseases. Recent advances in recombinant DNA technology enables the synthesis of a large variety of pharmaceutical proteins (Nagle et al., *Nature Rev. Drug Discov.*, vol. 2, pp. 75-79, 2003; Brekke et al., *Nature Rev. Drug Discov.*, vol. 2, pp. 52-62, 2003); however, broad use of the protein therapy is still limited by several substantial technical barriers, such as low efficiency of intracellular delivery and poor stability of protein against proteases.

Intracellular use of therapeutic proteins is of great importance for treatments of cancers and protein-deficient diseases (Wadia et al., *Protein Transport (Cell-penetrating peptides: Processes and Applications*, (CRC Press), p. 365, 2002). However, compared with the wide applications of extracellular active proteins, intracellular active protein drugs are rare in clinical applications (Birch et al., *Therapeutic Proteins, methods and Protocols*, (Humana Press, Totowa), pp. 1-16 2005), partially due to their poor stability in serum and weak permeability through cell membrane. Although some proteins can be translocated from the extracellular space into cells by receptor-mediated endocytosis (Vyas et al., *Crit. Rev. Ther. Drug Carrier Syst.*, vol. 18, pp. 1-76, 2001; Sato et al., *Adv. Drug Deliv. Rev.*, vol. 19, pp. 445-467, 1996), they may be entrapped within the endosome and degraded in the lysosome rather than be released to the appropriate cellular compartment. There is a growing effort to circumvent this problem. For example, liposome-wrapped proteins were shown to be transferred into the cytoplasm but with a low efficiency (Straubinger et al., *FEBS Lett.*, vol. 179, pp. 148-154, 1985; Bulmus et al., *J. Control Release*, vol. 93, pp. 105-120, 2003). Recently, several small cationic peptides (termed cell-penetrating peptides, CPPs) were identified and used to assist protein delivery (Fawell et al., *Proc. Natl. Acad. Sci. USA*, vol. 91, pp. 664-668, 1994; Morris et al., vol. 19, pp. 1173-1176, 2001; Schwarze et al., *Science*, vol. 285, pp. 1569-1572, 1999). With significantly improved intracellular delivery efficiency and retained activity in cells, this strategy is promising for pharmaceutical application. In addition, although one can deliver proteins into cells with these strategies, the poor stability of proteins within the cells still hampers the wide applications of therapeutic proteins. Among various possible inactivation factors (Fagain et al., *Biochim. Biophys. Acta.*, vol. 1252, pp. 1-14, 1995), protease digestion in serum is a crucial one, which needs to be addressed to ensure a successful intracellular protein delivery (Hooper, N. M. *Proteases in Biology and Medicine*, (Portland Press, London), 2002).

SUMMARY

Aspects of the invention include protein nanocapsules having a single-protein core and a thin polymer shell anchored covalently to the protein core. In some embodiments, the single-protein core is a protein having a plurality polymerizable groups. In some embodiments, the single-protein core is a protein catalyst. In some embodiments, the nanocapsule retains the catalytic activity of the protein core.

In some embodiments, the single-protein core is copolymerized with at least one monomer to form the nanocapsule. In other embodiments, the single protein core is copolymerized with at least one monomer and at least one crosslinker.

In some embodiments, the nanocapsule further includes a surface modification. The surface modifier may be a light-emitting molecule, a cell-targeting moiety, a peptide, a protein, an antibody or an oligosaccharide. The surface modifier may function as an imaging agent, a cell targeting enhancer, or a cell-penetration enhancer.

Other aspects of the invention include methods of preparing a nanocapsule by derivatizing a protein with at least one polymerizable group and then copolymerizing the derivatized protein with a monomer unit. In some embodiments, the copolymerization further includes a crosslinker. In some embodiments, the method further includes modifying the surface of the nanocapsule.

Other aspects of the invention include methods of delivering a protein by exposing a cell to an effective concentration of the nanocapsules described above.

BRIEF DESCRIPTION OF THE DRAWINGS

FIG. 2A shows native EGFP (1) and modified EGFP (2). FIG. 2B shows native HRP (1) and modified HRP (2). FIG. 2C shows native SOD (1) and modified SOD (2). FIG. 2D shows native Caspase-3 (1) and modified Caspase-3 (2).

FIG. 4A shows TEM images of HRP nanoparticles. FIG. 4B shows AFM images of HRP nanocapsules. FIG. 4C shows TEM image of nanocapsules containing a single 1.4-nm gold-quantum-dot-labelled HRP core. These figures confirm the formation of a single-core nanoscale architecture.

FIG. 6A shows zeta potential distribution of the nanocapsules fabricated with different monomer weight ratio (from top to bottom: DMAEMA (2)/AAm (1)=0, 1/3, 1). FIG. 6B shows zeta potential distribution of nHRP fabricated with different monomer weight ratio (from top to bottom: monomer 2 to monomer 1=1/6, 1/3, 1, zeta potential: 2.23, 5.83 to 10.93 mV).

FIG. 8A shows a comparison of fluorescence intensity of the native EGFP and EGFP nanocapsules after exposure to 1 mg/mL trypsin and chymotrypsin at 50° C. suggesting the EGFP nanocapsules are highly stable against protease (the fluorescence intensities were normalized to untouched EGFP before the exposure to proteases). FIG. 8B shows cellular fluorescence intensity of HeLa cells after incubation with 400 nM EGFP nanocapsules for 3, 48, and 144 hours showing decreasing intensity due to cell propagation. FIG. 8C shows cellular fluorescence intensity of HeLa cells after incubation with 400 nM TAT-EGFP fusion proteins for 3 hours indicating a rapid degradation of the unmodified protein. FIG. 8D shows cellular fluorescence intensity of cells after treatment with nEGFP or TAT-EGFP fusion proteins at different times.

FIG. 12A shows Fluoresence-assisted cell sorting of HeLa cells incubated with different concentrations of nEGFP (11.7 nm, zeta potential 10.9 mV), TAT-EGFP fusion proteins or native EGFP. FIG. 12B shows cellular fluorescence distribution of HeLa cells after treatment with naive EGFP, EGFP nanocapsules (nEGFP), antenapedia-EGFP conjugates (ANTE-EGFP). FIG. 12C shows correlations between zeta potential of EGFP nanocapsules and average cellular fluorescence intensity of HeLa cells after 3-hour co-culture with EGFP nanocapsules.

FIGS. 13A and 13B shows Hela cell fluorescence intensity after incubation with nEGFP for different times. HeLa cells were incubated with 400 nM nEGFP for different time, washed, trypsinized and subjected to FACS analysis.

FIG. 18A shows confocal images of HeLa cells after transduction of rhodamine-B-labelled nHRP (red), nEGFP (green), and NIR-667-labelled nBSA (blue). FIG. 18B shows Co-localization quantification of nEGFP, NIR-667-labeled nBSA, and rhodamine-B-labeled nHRP after these nanocapsules were simultaneously transducted into HeLa cells.

FIG. 21A shows MTT assay showing HeLa cell viability after transduction with 400 nM native HRP or nHRP and incubation with IAA for 12 h. Cell proliferation rates were normalized to untreated cells. FIG. 21B shows HeLa cell viability after incubation with nSOD and paraquat. Untreated cells were used as the 100% cell proliferation control and cells treated with paraquat only were used as the 0% control. Data represent averages, with error bars from three independent experiments performed in triplicate.

FIG. 23A shows the size of degradable CAS nanocapsules (de-nCAS) and non-degradable CAS nanocapsule (nCAS) at pH 5.5. FIG. 23B shows the size of degradable CAS nanocapsules (de-nCAS) and non-degradable CAS nanocapsule (nCAS) at pH 7.4.

DETAILED DESCRIPTION

Figure 1:
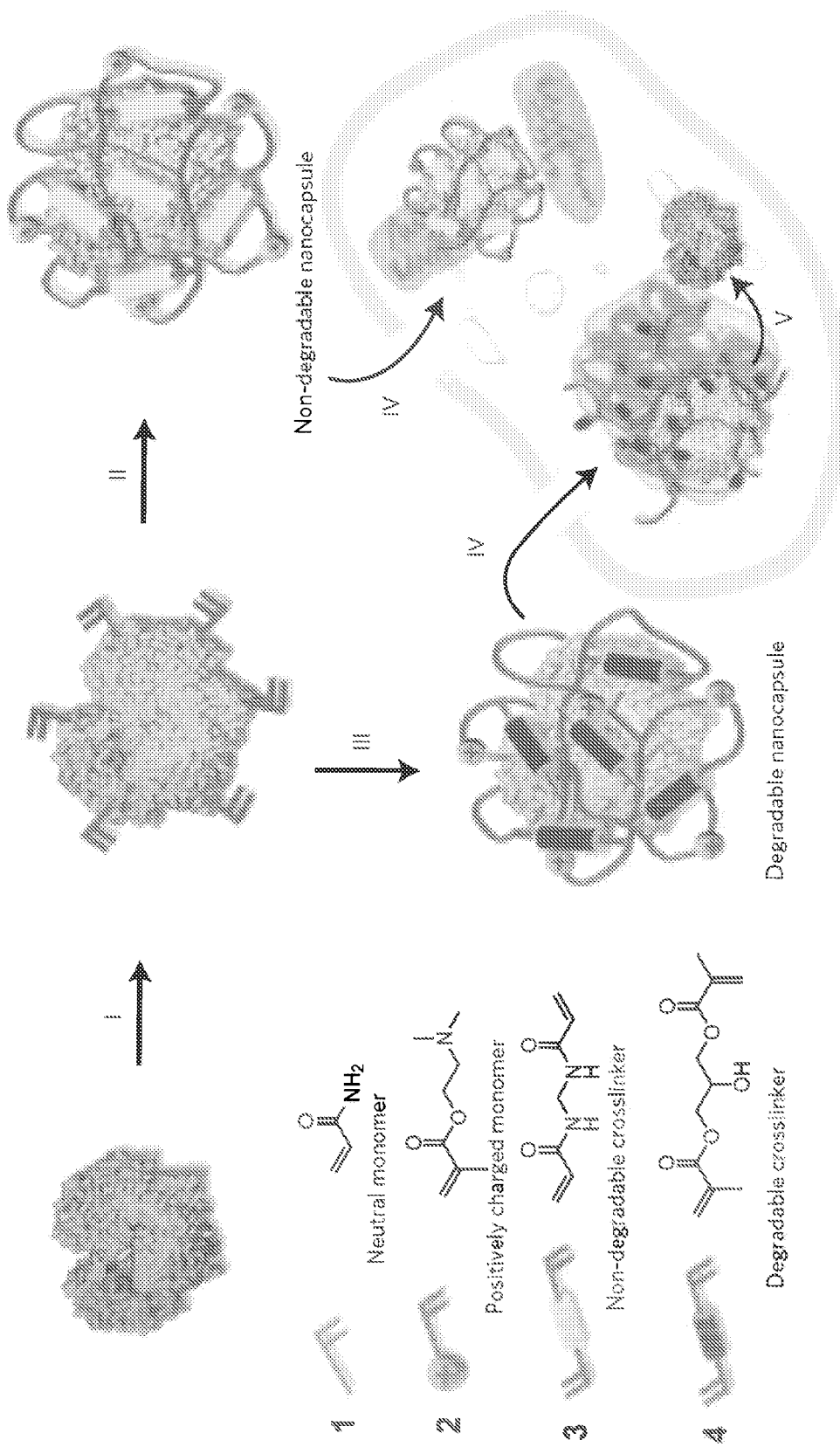
FIG. 1 is a schematic showing the synthesis and cellular uptake of exemplary cationic single-protein nanocapsules with degradable and non-degradable polymeric shells prepared by in situ co-polymerization of acrylamide (1), 2-dimethylaminoethyl methacrylate (2) and non-degradable crosslinker methylenebisacrylamide (3) or acid-degradable glycerol dimethacrylate (4): I, formation of polymerizable proteins by conjugating polymerizable acryl groups to the protein surface; II, formation of non-degradable nanocapsules from 1, 2 and 3; III, formation of degradable nanocapsules from 1, 2 and 4; IV, cellular uptake of the degradable or non-degradable nanocapsules via endocytosis; V, shells of degradable nanocapsules break down after internalization to release the protein cargoes, allowing them to interact with large molecular substrates.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Where a range of values is provided in the present application, it is understood that each intervening value, to the tenth of the unit of the lower limit unless the context clearly dictates otherwise, between the upper and lower limit of that range and any other stated or intervening value in that stated range, is encompassed within the invention. The end values of any range are included in the range.

Embodiments of the invention include a nanocapsule having a single-protein core and a thin polymer shell anchored covalently to the protein core. In some embodiments, the nanocapsule has a positive charge. In some embodiments, the nanocapsule may have a maximum dimension between about 5 nm and about 200 nm. The size may vary depending on the size of the single-protein core and the thickness of the thin polymer shell. The small size and charge result in high intracellular efficiency. Each nanocapsule contains two covalently-linked parts; a single-protein core and thin polymer network shell. That core-shell structure protects protein from proteolysis and thermal denaturation and is the origin of high stability in vivo or in vitro.

As used herein, the single-protein core means that the nanocapsule includes a single functional protein with the thin polymer shell. Frequently, the single functional protein is a single polypeptide. If the protein of interest normally functions as a multimer (i.e., dimer, homodimer, heterodimer, trimer, etc), then the single-protein core includes the multimer. For example, the active form of caspase-3 (CAS) is a dimer, and nanocapsules containing caspase-3 include the dimer as the single-protein core. Fusion proteins having multiple functions may also be used in the single-protein core, but multiple proteins which do not normally interact with each other to form a functional unit, are not a single-protein core. Multiple copies of the same protein, which do not normally associate to form a functional unit, are not a single-protein core.

The nanocapsules have a discrete size and low size distribution. The single-protein core is encapsulated in the polymer coating. In some embodiments, the polymer coating is crosslinked to increase the density of the polymer coating encapsulating the protein. In some embodiments, the polymer is covalently anchored to the thin polymer shell in at least 3, 4, 5, 7, 10, 15, or 20 locations on the protein. In some embodiments, the polymer is covalently anchored to the thin polymer shell in at least 3 locations. This ensures that the protein is encapsulated in the polymer network.

In some embodiments, the nanocapsule may have a maximum dimension between about 5 nm and about 200 nm. The size of the nanocapsule depends, in part, on the size of the single-protein core and the thickness of the thin polymer shell. In some embodiments, the nanocapsule may be between about 10 nm and about 200 nm, between about 5 nm and about 100 nm, between about 5 nm and 50 nm, or between about 10 nm and about 30 nm. In some embodiments, the polymer shell may be between about 1 nm and about 20 nm thick. In some embodiments, the polymer shell may be between about 1 nm and about 10 nm thick. In some embodiments, the nanocapsules are roughly spherical, though the shape may vary, depending on the shape of the single-protein core. As an example, a single-protein core with a diameter of about 5 nm (such as, for example, enhanced green fluorescence protein (EGFP)), with a polymer shell about 2 nm thick would have an overall size of about 9 nm.

In some embodiments, the protein may be a protein catalyst (i.e. an enzyme). In some embodiments, the protein may have another function, such as light emission (e.g., EGFP). Chemically or covalently modified proteins may also be used, as desired, so long as the modification does not interfere with formation of the nanocapsule. In general, any protein may be incorporated into the nanocapsule according to the invention, and selected based on the utility of the protein. In some embodiments, the protein is useful in cosmetic or therapeutic applications. Exemplary examples of proteins used to fashion nanoparticles include enhanced green fluorescent protein (EGFP), horseradish peroxidase (HRP), superoxide dismutase (SOD), bovine serum albumin (BSA), caspase-3, and lipase. Chemically modified proteins, such as rhodamine-B-labeled HRP, and NIR-667-labeled BSA have also been used. Examples of specific proteins for a variety of different applications are given in the following table. Other examples of proteins will be apparent to one of ordinary skill.

| For cosmetic applications | |
|---|---|
| Photolyase | Prevention of genome-damaging effects caused by ultraviolet (UV) radiation. |
| Superoxide Dismutase (SOD) | Antioxidant that protects oxygen-metabolizing cells against harmful effects of superoxide free radicals. |
| Botulinum toxin | Improvement of the look of the moderate-to-severe frown lines between the eyebrows (glabellar lines). |
| For therapeutic applications | |
| Horseradish peroxidase (HRP) | Enzyme-mediated prodrug cancer therapy used in combination with indole-3-acetic acid. |
| Thymidine kinase from herpes simplex virus (HSV-TK) | Enzyme-mediated prodrug cancer therapy used in combination with Ganciclovir |
| Caspases | Cancer Therapy Based on Restoration of Endogenous Cell Death Mechanisms |
| Vascular endothelial growth factor (VEGF) | Inducing Angiogenesis for trauma healing |
| Urate oxidase | Treatment for gout. |

-continued

| | |
|---|---|
| β-Glucosidase, (β-hexosaminidase | Enzyme replacement therapy for lysosomal storage diseases (Gaucher's and Fabry's disease) |
| Murine anti-CD3 antibody | Prevention of organ transplant rejection |

In some embodiments, the polymer shell is permeable. As used herein, permeable means that molecules may pass through the polymer shell, either through pores or holes in the polymer shell, or by diffusion through the polymer. For example, substrates, co-factors and other chemical elements may pass through the polymer shell, allowing the nanocapsule to retain the activity of the single-protein core.

Proteins in these nanocapsules are more stable than unmodified proteins. Stability is determined in the loss of protein activity over time or degradation or denaturation of the protein. In some embodiments, the nanocapsules are resistant to degradation by proteases. The thin polymer shell reduces exposure of the protein core to protease enzymes. As a result, the activity of the protein core lasts longer in the presence of proteases (for example, in vivo, in serum, or in cells) than unprotected native proteins. The thin polymer shell stabilizes the protein structure, and prevents aggregation of the protein. Thus, nanocapsules are more resistant to changes in pH and temperature. For example, nanocapsules have a longer storage lifetime at room temperature or decreased temperature (i.e. refrigeration or freezing), than native proteins. Likewise, nanocapsules are less likely to lose activity after multiple freeze/thaw cycles than native proteins. Because the protein structure is stabilized by the thin polymer shell, the nanocapsules are more resistant to organic solvents and surfactants. The polymer coating may also be adjusted to increase solubility in organic solvents. Examples of organic solvents and surfactants that may be used with the nanocapsules include methanol, ethanol, isopropyl alcohol, dimethyl sulfoxide, tetrahydrofuran, 4-dichlorobenzene, para-dichlorobenzene, 1,4-dioxane, 1,4-dioxane PEG, polyethylene, polyethylene glycol, polyoxyethylene, sodium laureth sulfate or oxynol, polysorbate 60, 2-bromo-2-nitropropane-1,3-diol, 2-butoxy-1-ethanol, alkyl phenoxy, polyethoxy ethanol, among others widely used in cosmetics (i.e. make-up) and pharmaceuticals. Other organic solvents will be apparent to one of ordinary skill in the art. Because the thin polymer coating prevents aggregation, the nanocapsules are more stable at interfaces (i.e. gas/liquid or liquid/solid) where unprotected proteins tend to aggregate.

In some embodiments, the nanocapsule retains the activity of the single-protein core. Where the single-protein core is fluorescent (e.g. EGFP, or fluorescently labeled BSA), the nanocapsule is also fluorescent. Where the single-protein core is enzymatically active, the enzymatic activity is present in the nanocapsule. The activity of the nanocapsule may be reduced, relative to the single-protein core without the polymer shell. In some embodiments, the activity of the nanocapsule is at least about 30% of the native protein. In other embodiments, the activity of the nanocapsule is at least about 50% of the native protein, at least about 70% of the native protein, or at least about 90% of the native protein.

In some embodiments, the single-protein core is a protein having a plurality of polymerizable groups. A polymerizable group is a chemical moiety that polymerizes under certain chemical conditions. Examples of polymerization conditions include photopolymerization, free radical polymerization, and catalyst induced polymerization. In general, the type of polymerizable group is not critical, so long as the polymerizable group is capable of polymerization with a monomer used to form the nanocapsule. Examples of polymerizable groups include double-bond containing moieties which are polymerized by photopolymerization or free radical polymerization. In some embodiments, the polymerizable group is a vinyl group, acryl group, alkylacryl group (i.e. acryl group having an alkyl substituent, such as methacryl). As used herein, acryl (alkylacryl, methacryl, etc) includes acryl esters as well as acryl amides. In some embodiments, the polymerizable group is an acryl group covalently bonded to a lysine residue of the protein core.

Proteins contain many different surface amino acids which can readily be modified. For example, lysine, cysteine, threonine, glutamic acid, aspartic acid, serine, histidine, arginine, tyrosine, proline and tryptophan may be readily modified using known processes and procedures. A reagent used to modify the protein will have at least one polymerizable group, and at least one reactive group that reacts with an amino acid side-chain on the surface of the protein. Examples of reactive groups that are used to react with amino acid side chains include activated esters (such as acyl halides or N-hydroxysuccinimide esters) that react with amine (such as lysine) and hydroxyl (such as threonine or serine) containing residues; maleimides that react with thiol (such as cysteine) containing residues; and amines which react with carboxylic acid (such as glutamic acid and aspartic acid) containing residues when activated with certain coupling reagents. This way, the polymerizable group is covalently bonded to the single-protein core. The polymerizable group may be directly bonded, or attached through a linker.

In some embodiments, a linker is present between the protein core and the polymerizable group. The linker is a chemical moiety separating the polymerizable group, and the protein core. A reagent used as a linker will have at least one polymerizable group, and at least one reactive group separated by a linker. The reactive group reacts with the protein core, usually by reaction with an amino acid side chain on the surface of the protein, covalently bonding the polymerizable group to the single-protein core with the linker between them.

In some embodiments, the linker may be degradable. A degradable linker is a chemical moiety that is cleaved under certain conditions. For example, a degradable linker may, for example, hydrolyze at certain pH values (high pH or low pH), or may be cleaved photolytically (i.e. when irradiated with light of certain wavelengths), or under certain temperatures, under reduction-oxidation conditions, or enzymatically (i.e. by proteases). Any suitable degradable linker may be used, so long as the linker has a reactive group to react with the protein core, and a polymerizable group to form the nanocapsule. The degradable linker should also be stable during polymerization of the nanocapsule. The type of linker may be selected based on the conditions under which the linker will be cleaved. Numerous linkers are known, and will be readily apparent to one of ordinary skill.

In some embodiments, the nanocapsule is a single-protein core co-polymerized with a monomer unit. A monomer unit is a chemical moiety that polymerizes and forms a co-polymer with the single-protein core, forming the polymer shell of the nanocapsule. In some embodiments, when the single-protein core bears polymerizable groups having a double bond, such as a vinyl, acryl, alkylacryl or methacryl group, the monomer unit also has a polymerizable group having double bond, such as a vinyl, acryl, acrylamido, alkylacryl, alkylacrylamido, methacryl or methacrylamido group. The polymerizable group of the protein, and the polymerizable group of the monomer unit may be the same or different, so long as they are capable of forming a co-polymer under the conditions used to form the nanocapsule. For example, vinyl and acryl groups may form co-polymers under free-radical polymerization conditions.

In some embodiments, the nanocapsule is a single protein core co-polymerized with two or more different monomer units. In general, any number of different monomer units may be used to form co-polymers with the protein core, so long as the different monomer units are all capable of forming a co-polymer under the conditions used to form the nanocapsule. Monomer units with different side-chains may be used to alter the surface features of the nanocapsule. The surface features may be controlled by adjusting the ratio between different monomer units. In some embodiments, the monomer may be neutral, neutral hydrophilic, hydrophobic, positively charged, or negatively charged. Solubility of the nanocapsule may be adjusted, for example, by varying the ratio between charged and uncharged, or hydrophilic or hydrophobic monomer units. In some embodiments, the nanocapsule has a positive or negative charge.

In some embodiments, at least one monomer unit has a positive or negative charge at pH=7.4. By using monomer units having a charge at pH=7.4, the overall charge of the nanocapsule may be varied and adjusted by changing the ratio of the charged and uncharged monomer units. In some embodiments, the monomer unit has a positive charge at pH=7.4. Using positively charged monomer units enables the formation of nanocapsules having a positive charge. The charge may be adjusted by changing the ratio of neutral and positively charged monomer units.

In some embodiments, the nanocapsule comprises a single-protein core copolymerized with at least one monomer unit (as described above) and at least one crosslinker. A crosslinker is a chemical compound having two or more polymerizable groups. In general, any crosslinking compound may be used, so long as the polymerizable groups on the crosslinker are capable of forming a crosslinked co-polymer between the protein core and the at least one monomer unit under the conditions used to form the nanocapsule. Examples of crosslinkers include compounds having two vinyl, acryl, alkylacryl, or methacryl groups. Examples of specific crosslinkers having two acryl groups include N,N'-methylenebisacrylamide and glycerol dimethacrylate (both shown in FIG. 1).

In some embodiments, the crosslinker is a degradable crosslinker. A degradable crosslinker is cleaved under certain conditions, resulting in decomposition or removal of at least a portion of the polymer shell of the nanocapsule. For example, a degradable crosslinker may hydrolyze at certain pH (high or low), may be cleaved by specific enzymes (such as esterases or peptidases), may be photolytically cleaved upon exposure to certain wavelengths, or be cleaved at certain temperatures. Examples of crosslinkers which hydrolyze at reduced pH include glycerol dimethacrylate, which is stable at physiological pH (about 7.4), but hydrolyzes at lower pH (about 5.5). Other examples of degradable crosslinkers include acetal crosslinkers described in U.S. Pat. No. 7,056, 901, which is incorporated by reference in its entirety.

Further specific examples of degradable and non-degradable crosslinking groups are given in the following table.

| Degradability | Name | Structure |
|---|---|---|
| Non-degradable | N,N'-Methylenebis(acrylamide) | 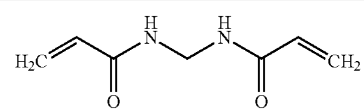 |
| | 1,4-Bis(acryloyl)piperazine | |
| | Ethylene glycol diacrylate | |
| | N,N'-(1,2-Dihydroxyethylene)bisacrylamide | |
| | Poly(ethylene glycol) diacrylate | |
| Redox-degraded | N,N'-Bis(acryloyl)cystamine | 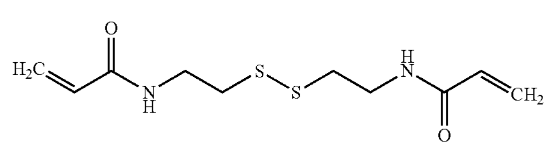 [SMILES: C=CC(=O)NCCSSCCNC(=O)C=C] |

-continued

| Degradability | Name | Structure |
|---|---|---|
| Acid-Degraded | Glycerol dimethacrylate | (structure shown); R = H or * |
| | Bis[2-(methacryloyloxy)ethyl] phosphate | (structure shown) |
| Protease-degraded | bisacryloylated polypeptide | NH₂ Ala-Ala-Pro-Val-Ala-Ala-Lys (with bisacryloyl groups) |

In cases where the substrate of the protein core is too large to pass through the polymer coating, a degradable crosslinker that removes or reduces the polymer coating may be advantageous. For example, a degradable crosslinker that decomposes at reduced pH may be used to remove or reduce the polymer coating after the nanocapsules are internalized into cells by endocytosis. It is well known that serum and late endosomes have pH values of ~7.4 and ~5.5, respectively. Thus, a degradable crosslinker that is stable at pH ~7.4, but degrades at pH ~5.5 will remove or reduce the polymer coating only after the nanocapsule has entered the cell. In this way, the protein core is protected from proteases present in serum, but protein cores with large substrates may still be effectively delivered to cells. After the polymer coating is reduced, the activity of the protein core is still present. After the polymer coating is removed, however, the protein core becomes susceptible to degradation by intracellular proteases, but this drawback is offset by the nanocapsule's increased stability in serum, and resistance to serum proteases.

In certain embodiments, the nanocapsule further includes a surface modification. Surface modifications are chemical moieties which are added to the surface of the nanocapsule after formation of the nanocapsule. Monomer units having reactive sidechains (or protected reactive sidechains) may be used to form the nanocapsule so long as the reactive sidechains do not interfere with formation of the nanocapsule. The reactive sidechains may be (after deprotection, if necessary) reacted with surface modifying agents to covalently attach the surface modification to the nanocapsule. A surface modifying agent may be a small molecule, polymer, peptide, polypeptide, protein, oligonucleotide, polysaccharide, or antibody. The surface modification may alter the solubility of the nanocapsule, change the surface charge of the nanocapsule, or impart an additional function to the nanocapsule, such as light-emission, cell targeting or cell penetration. Surface modifications that enhance cell targeting result in an increased transduction of the nanocapsule into targeted cells, when compared with non-targeted cells. Surface modifications that enhance cell penetration result in increased transduction of nanocapsules into cells when compared with nanocapsules lacking the cell penetration enhancer. More than one surface modification may be present on the nanocapsule. Examples of small molecule surface modifications include light emitting compounds, such as fluorescein, or rhodamine, or cell targeting compounds such as folic acid. Polymers include polyethylene glycol to increase solubility. Peptides may be used for cell targeting, such as antibodies to particular cell surface features, cell signaling proteins, or growth hormones. Other peptides may be used to increase cell penetration of the nanoparticles (such as TAT or antennepedia homeodomain). In some embodiments, the surface modification is an antibody.

Production

Embodiments of the invention include methods of producing nanocapsules having a single-protein core and a thin polymer shell anchored covalently to the protein core derivatizing a protein with at least one polymerizable group; and then copolymerizing the derivatized protein with a monomer unit.

A general two-step procedure is used to fabricate single-protein nanocapsules. First, polymerizable groups are covalently linked to the protein surface. Then subsequent polymerization of functional monomers and optionally, crosslinkers, in buffer solution wraps each of the protein cores with a thin (crosslinked network) polymer skin. This general method enables the facile synthesis of a large variety of low-size-distributed nanocapsules with desired protein cores and easy control of surface charge and functional groups.

Once the polymerizable groups are attached to the enzyme surface, monomers (for example, those listed in Table 2) can be used to form polymer coatings with tunable composition, structure, surface property, and functionality. A room temperature free-radical polymerization technique may be used to ensure the retention of enzyme activity. Since these polymer coatings serve as artificial membranes for the encapsulated enzymes, they exhibit suitable mechanical strength to provide structural integrity, possess effective transport pathways to allow rapid substrate transport, and contain specific functionality to provide substrate selectivity and moisture retention.

Nanocapsules do not change the biofunctions of the protein cores, which may be obtained directly from commercial sources or using other reported methods.

A reagent used to derivatize or modify the protein has the following general structure

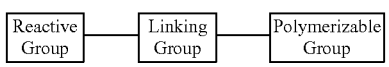

where the polymerizable group is a chemical moiety that forms a copolymer with one or more monomers and/or crosslinkers under conditions used to form the nanocapsule. In some embodiments, the polymerizable group is a double bond containing group, such as vinyl, acryl, alkylacryl, and methacryl. As discussed previously, acryl (and alkylacryl and methacryl) includes both acryl esters and acrylamides.

A linking group is optional and may be present between the polymerizable group and the protein. The linking group is a chemical moiety that separates the reactive group from the polymerizable group. The linking group is not limited to any particular chemical structure, but should not interfere in the polymerization reaction. In some embodiments, the linking group is a degradable linking group, which is cleaved under certain conditions. For example, acetals, ketals or esters may be hydrolyzed at certain pHs. Linking groups having one or more of these functional groups may decompose in response to changes in pH (e.g. in endosomes, as discussed above).

A reactive group is a chemical moiety that reacts with an amino acid side chain to covalently attach the polymerizable group to the protein. Numerous reactive groups are known and are used to react with different amino acid side chains. For example, acyl halides, or activated esters (such as N-hydroxysuccinimide esters) react with amines (e.g. on lysine) or hydroxyls (e.g. on serine or threonine). Isocyanates react with amines. Epoxides react with amines or thiols (e.g. cysteine). Maleimides react with thiols. Other functional groups may react with amino acid side chains in the presence of one or more coupling reagents (such as carbodiimide reagents). For example amines may react with carboxylic acid amino acid side chains (e.g. on glutamate or aspartate). Other reactive groups will be readily apparent to one of ordinary skill in the art.

During the protein modification mentioned above, to realize the site-specific controlled modification, a genetic recombinant technique can be used to introduce specific amino acids in spatially defined locations. This technique allows precise control of the site and density of the modification.

Examples of specific compounds used to derivatize proteins are shown in Table 1. Numerous other examples are available, and will be apparent to one of ordinary skill in the art.

TABLE 1

Reagents used for protein surface modification

| Amino Acid | Modification Reagents | |
|---|---|---|
| Lysine | N-acryloxysuccinimide | 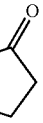 |
| | Glycidyl acrylate | |
| Cysteine | N-(p-allylcarboxyphenyl) maleimide | |
| | N-(p-allylamidophenyl) maleimide | |
| Glutamic acid | Allyl amine | |
| Aspartic Acid | N-(3-aminopropyl) methacrylamide | |
| | 2-aminoethyl methacrylate | |

A monomer unit has the general structure

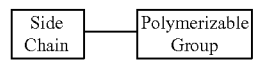

where the polymerizable group is a chemical moiety that forms a copolymer with the protein core and optional crosslinkers under conditions used to form the nanocapsule. Polymerizable groups include all those discussed previously. The polymerizable group of the protein, and the polymerizable group of the monomer unit may be the same or different, so long as they are capable of forming a co-polymer under the conditions used to form the nanocapsule. For example, vinyl and acryl groups may form co-polymers under free-radical polymerization conditions.

The side chain is a portion of the monomer unit that does not participate in polymerization. In general, the side chain may have any structure, and may be selected based on the desired properties of the nanocapsule. The side chains of the monomer unit affect the surface properties of the nanocapsule. In some embodiments, the side chain may be neutral, neutral hydrophilic (i.e. water soluble, but not charged), hydrophobic, positively charged, or negatively charged. Neutral side chains include amides, esters, ethers, hydroxyls some of which may be hydrophilic or hydrophobic, depending on their structure. Positively charged side chains include amines (including substituted amines, such as mono and dialkyl amines, and tetrasubstituted ammonium compounds, and cyclic variants thereof), guanidines, and heterocycles such as pyridines and imidazoles. Negatively charged sidechains include carboxylic acids. Hydrophobic side chains include alkyl groups (including linear, branched or cyclic alkyl groups) and aryl groups.

Examples of specific monomer units and their functions are given in table 2.

TABLE 2

Monomers used to form polymer coatings with tunable structure and functions

| Type | Monomers | | Function |
|---|---|---|---|
| Neutral | Acrylamide | $CH_2=CHCONH_2$ | 1 |
| | 2-Hydroxyethyl acrylate | $CH_2=CHCOOCH_2CH_2OH$ | |
| | N-isopropylacrylamide | $CH_2=CHCONHCH(CH_3)_2$ | 2 |
| Negatively charged | Sodium acrylate | $CH_2=CHCOONa$ | 3 |
| | 2-Acryloylamido-2-methylpropanesulfonic sodium | $CH_2=CHCONHC(CH_3)_2CH_2SO_3Na$ | |
| Positively charged | Allyl amine | $CH_2=CHCH_2NH_2$ | 4 |
| | N-(3-Aminopropyl) methacrylamide hydrochloride | $CH_2=C(CH_3)CONH(CH_2)_3NH_2 \cdot HCl$ | 4, 5 |
| | Dimethylamino ethyl methacrylate | $CH_2=C(CH_3)COCH_2CH_2N(CH_3)_2$ | 5 |
| | (3-Acrylamidopropyl) trimethylammonium hydrochloride | $CH_2=C(CH_3)CONH(CH_2)_3N(CH_3)_3Cl$ | |
| Hydrophobic | Methyl acrylate | $CH_2=CHCOOCH_3$ | 6 |
| | Styrene | $CH_2=CHC_6H_5$ | |

Functions: 1 to 5: hydrophilic surface and moisture retention;
2) temperature responsive;
3) negatively charged surface;
4) reactive sidechain for surface modification,
5) positive charge surface,
6) hydrophobic surface.

Polymerization of the modified protein and monomer unit(s) may use any method suitable for the polymerizable groups used on the protein and monomer unit(s) and which does not destroy the function of the protein during polymerization. Examples of polymerization methods include photopolymerization and free-radical polymerization of double bond containing polymerizable groups, such as those described previously. In some embodiments, the polymerization is a free radical polymerization.

In some embodiments, the polymerization is carried out at room temperature, though the temperature may be increased or decreased as desired, depending on the polymerization method, so long as the function of the protein is not lost during polymerization. Where degradable crosslinkers or linking groups are used, the function of the nanoparticle may be measured after degradation of the polymer coating. Reaction temperatures may be increased where the polymerization reaction occurs too slowly, or where elevated temperature are needed to initiate polymerization. Temperatures may be decreased where polymerization reactions occur too quickly.

In some embodiments, the polymerization reaction is performed in water, or aqueous buffer. Other solvents may be used as desired, so long as the solvent does not interfere with the polymerization reaction, or degrade the protein. Mixtures of water or aqueous buffer and organic co-solvents may also be used, if necessary to dissolve reaction components, so long as the solvent mixture does not interfere with the reaction, or damage the protein core. In some embodiments, the polymerization reaction is performed in buffer.

In some embodiments, the copolymerization step comprises at least two different monomer units. In general, any number of different monomer units may be used to form co-polymers with the protein core, so long as the different monomer units are all capable of forming a co-polymer under the conditions used to form the nanocapsule. Monomer units with different side-chains may be used to alter the surface features of the nanocapsule. The surface features may be controlled by adjusting the ratio between different monomer units. In some embodiments, the monomer may be neutral, neutral hydrophilic, hydrophobic, positively charged, or negatively charged. Solubility of the nanocapsule may be adjusted by varying the ratio between charged and uncharged, or hydrophilic or hydrophobic monomer units.

In some embodiments, the copolymerization step further includes a crosslinker. A crosslinker is a reagent having at least two polymerizable groups, separated by a linking group. The crosslinker may have more than two polymerizable groups. The polymerizable groups on the crosslinker may be the same or different, so long as all the polymerizable groups on the crosslinker are able to form a copolymer with the monomer unit(s) and protein core under the conditions used to form the nanocapsule. A crosslinker having two polymerizable groups has the general structure

where the polymerizable groups are the same as those described previously. The linking group may have any structure so long as it does not interfere with the polymerization reaction. Examples of suitable linkers include alkyl groups (including substituted alkyl groups), aryl groups (including substituted aryl groups), ketones, amides, esters, ethers and combinations thereof. Specific examples of crosslinkers include N,N'-methylene bisacrylamide and glycerol dimethacrylate (See FIG. 1).

In some embodiments, the linking group is degradable. A degradable linking group may be cleaved under certain conditions. The structure of the degradable linking group determines the type of conditions required to cleave the linking group. For example, the linking group may be cleaved due to a change (i.e. increase or decrease) in pH, exposure to certain wavelengths of light, or in response to heat. An example of a degradable crosslinker is glycerol dimethacrylate.

In some embodiments, the method of producing a nanocapsule further includes a step of modifying the surface of the nanocapsule. Sidechains of the monomer unit(s) are present on the surface of the nanocapsule after polymerization. Monomer units having a reactive sidechain (or protected reactive sidechain) may be used to prepare the nanocapsule. The reactive sidechain does not interfere with polymerization, but may undergo further chemical modification after the nanocapsule is formed (i.e. after polymerization is completed). A protected reactive sidechain may be deprotected using standard chemical deprotection methods, then reacted with a chemical modifying agent. A reactive sidechain is treated with a chemical reagent to covalently attach the surface modifying agent to the surface of the nanocapsule. The surface modification may be a small molecule, polymer, peptide, polypeptide, protein, oligonucleotide, polysaccharide, or antibody. The surface modification may alter the solubility of the nanocapsule (e.g. by adding polyethylene glycols or other hydrophilic groups), change the surface charge of the nanocapsule (e.g. by adding charged surface modifiers), or impart an additional function to the nanocapsule, such as light-emission, cell targeting or cell penetration. Examples of small molecule surface modifications include light emitting compounds, such as fluorescein, or rhodamine, or cell targeting compounds such as folic acid. Polymers include polyethylene glycol to increase solubility. Peptides and polypeptides may be used for cell targeting, and may include antibodies selective to specific cell surface features, cell signaling peptides, or hormones. Other peptides may be used to increase cell penetration of the nanoparticles (such as TAT or antennepedia homeodomain). In some embodiments, the surface modification is an antibody. Because nanocapsules have an easily derivatized surface, specific antibodies can be conjugated with nanocapsules providing extra ability of targeting delivery.

Figure 6:
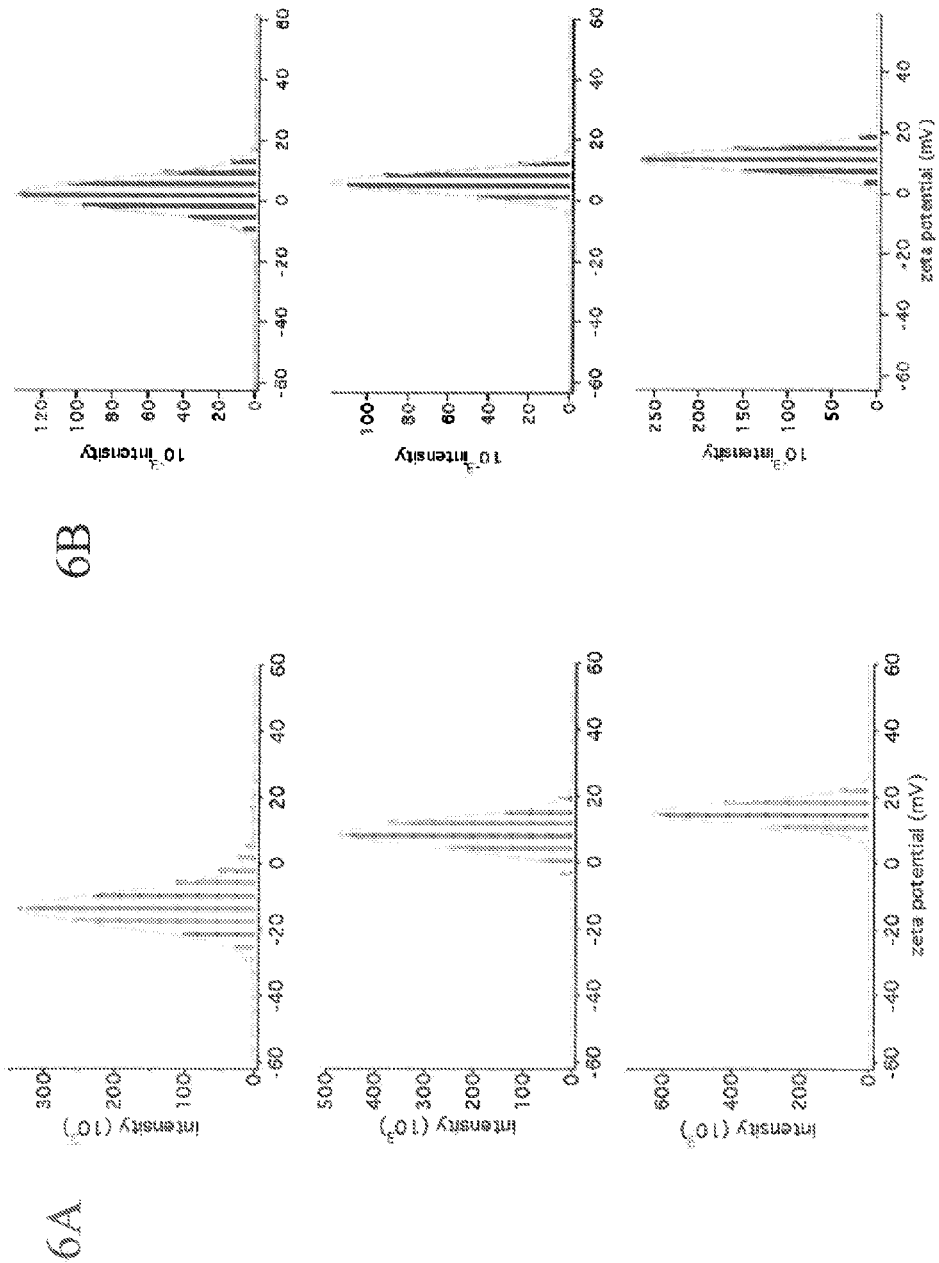
FIG. 6 shows effect of monomer weight ratio on zeta potential.

The size and surface features of the nanocapsules may be adjusted by varying the weight ratio of the different monomers and/or crosslinkers used to form the nanocapsule. For example, tuning the weight ratio of DMAEMA (positive charged) to AAm (neutral) from 0:1, 1:3 and 1:1 allows the synthesis of BSA nanocapsules with adjustable zeta potentials from −12.8, 8.64 to 15.2 mV (FIG. 6A), respectively. Solubility may also be easily adjusted by changing the types and ratios of monomer units and crosslinkers. Increasing the amount of hydrophilic or charged monomers increases water solubility. Increasing the amount of hydrophobic monomers tends to increase nanocapsule solubility in organic solvents or mixed organic/water solvent systems.

The permeability of the thin polymer coating may be adjusted by varying the ratio of the crosslinker in the reaction mixture used to prepare the nanocapsule. In general, a lower amount of crosslinker results in a higher permeability. Likewise, the permeability of the thin polymer coating may be varied by changing the length of the linking group on the crosslinker. Generally, longer linking groups lead to increased permeability.

This simple method provides an effective route to the preparation of novel protein-intracellular-delivery vectors with well-controlled size, surface features and using any protein core.

Uses

Nanocapsules play very similar intracellular functions as the proteins incorporated inside. A large variety of proteins can be used to form nanocapsules which play different functions. Exemplary bioactive proteins tested include enhanced green fluorescent protein (EGFP), horseradish peroxidase (HRP), bovine serium albumin (BSA), and superoxide dismutase (SOD).

The nanocapsules described herein may be used to deliver proteins or protein activity to a cell in vitro or in vivo with improved stability and/or long-term effect. Since the nanocapsules are more resistant to degradation by proteases, the protein activity has a longer effect than when native or unprotected proteins are administered. As a result, less protein (in the form of nanocapsules) is required for the same effect (when compared with unprotected proteins), thereby improving efficiency.

Embodiments of the invention include a method of delivering a protein by exposing a cell to an effective concentration of nanocapsules described above. The cells may be in culture (i.e. in vitro) or may be present in a living organism (i.e. in vivo). As used herein "delivering a protein" means delivering the activity of the protein to the cell, since the protein is modified to form the nanocapsules. However, the activity of the nanocapsule is the same as the activity of the native protein used in the nanocapsule. In instances where the protein substrate does not penetrate the nanocapsule, a degradable polymer coating may be used, delivering the protein to a cell after reduction or removal of the polymer coating.

In some embodiments, the protein is a therapeutic protein. A therapeutic protein is a protein or enzyme which is used to treat a disease or disorder in a subject. In some embodiments, the subject is a mammal, or a human.

The nanocapsules described herein may be used with any protein or enzyme that may be used to treat a disease or disorder in a subject. For example, nanocapsules according to the invention may be used in the treatment of a hyperproliferative disorder, cancer, or tumor. In other embodiments, the nanocapsules may be used in cosmetics.

Pharmaceutical Compositions

The nanocapsules discussed herein can be formulated into various compositions, for use in diagnostic or therapeutic treatment methods. The compositions (e.g. pharmaceutical compositions) can be assembled as a kit. Generally, a pharmaceutical composition of the invention comprises an effective amount (e.g., a pharmaceutically effective amount) of a composition of the invention.

A composition of the invention can be formulated as a pharmaceutical composition, which comprises a composition of the invention and pharmaceutically acceptable carrier. By a "pharmaceutically acceptable carrier" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18$^{th}$ ed., Mack Publishing Company, 1990. Some suitable pharmaceutical carriers will be evident to a skilled worker and include, e.g., water (including sterile and/or deionized water), suitable buffers (such as PBS), physiological saline, cell culture medium (such as DMEM), artificial cerebral spinal fluid, or the like.

A pharmaceutical composition or kit of the invention can contain other pharmaceuticals, in addition to the compositions of the invention. The other agent(s) can be administered at any suitable time during the treatment of the patient, either concurrently or sequentially.

One skilled in the art will appreciate that the particular formulation will depend, in part, upon the particular agent that is employed, and the chosen route of administration. Accordingly, there is a wide variety of suitable formulations of compositions of the present invention.

One skilled in the art will appreciate that a suitable or appropriate formulation can be selected, adapted or developed based upon the particular application at hand. Dosages for compositions of the invention can be in unit dosage form. The term "unit dosage form" as used herein refers to physically discrete units suitable as unitary dosages for animal (e.g. human) subjects, each unit containing a predetermined quantity of an agent of the invention, alone or in combination with other therapeutic agents, calculated in an amount sufficient to produce the desired effect in association with a pharmaceutically acceptable diluent, carrier, or vehicle.

One skilled in the art can easily determine the appropriate dose, schedule, and method of administration for the exact formulation of the composition being used, in order to achieve the desired effective amount or effective concentration of the agent in the individual patient.

The dose of a composition of the invention, administered to an animal, particularly a human, in the context of the present invention should be sufficient to effect at least a detectable amount of a diagnostic or therapeutic response in the individual over a reasonable time frame. The dose used to achieve a desired effect will be determined by a variety of factors, including the potency of the particular agent being administered, the pharmacodynamics associated with the agent in the host, the severity of the disease state of infected individuals, other medications being administered to the subject, etc. The size of the dose also will be determined by the existence of any adverse side effects that may accompany the particular agent, or composition thereof, employed. It is generally desirable, whenever possible, to keep adverse side effects to a minimum. The dose of the biologically active material will vary; suitable amounts for each particular agent will be evident to a skilled worker.

Another embodiment of the invention is a kit useful for any of the methods disclosed herein, either in vitro or in vivo. Such a kit can comprise one or more of the compositions of the invention. Optionally, the kits comprise instructions for performing the method. Optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form.

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Terms listed in single tense also include multiple unless the context indicates otherwise.

The examples disclosed below are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

Methods for preparing, characterizing and using the compounds of this invention are illustrated in the following Examples. Starting materials are made according to procedures known in the art or as illustrated herein. The following examples are provided so that the invention might be more fully understood. These examples are illustrative only and should not be construed as limiting the invention in any way.

EXAMPLES

Materials

All chemicals were purchased from Sigma-Aldrich unless otherwise noted, and were used as received. N-(3-Aminopropyl)methacrylamide hydrochloride was purchased from Polymer Science, Inc. Rabbit anti-EEA antibody and rabbit anti-Rab7 antibody were purchased from Cell Signaling Technology, Inc. Alexa488 goat anti-rabbit IgG and APO-BrdUTM TUNEL apoptosis kit were purchased from Invitrogen Life Technologies, Inc. Sulfhydryl-containing Cys(N-pys) antennapedia peptide were purchased from AnaSpec, Inc. 2-Dimethylaminoethyl methacrylate was purified with column chromatography before use and stored at −20° C. thereafter.

Instrumentation

IR spectra of the nanocapsules were obtained on a PerkinElmer Paragon 1000 FT-IR spectrometer. UV-Visible spectra were acquired with a GeneSys 6 spectrometer (Thermo Scientific). Fluorescence spectra were obtained with a QuantaMaster Spectrofluorimeter (Photon Technology International). TEM images of nanocapsules were obtained on a Philips EM120 TEM at 100000×. Before observation, nanocapsules were negatively stained using 1% pH 7.0 phosphotungstic acid (PTA) solution. Zeta potential and particle size distribution were measured with a Malvern particle sizer Nano-ZS. SEM images of nanocapsules were obtained with a JEOL JSM-6700F SEM. Dry samples on a silicon surface were sputter-coated with gold before measurement. AFM measurement of the sample was performed with a Nanoscope III (Digital Instruments, Santa Barbara, USA) operated in the tapping mode in air on a freshly cleaved mica surface. Fluorescent images of cells were obtained with either Zeiss Axio Observer.Z1 fluorescence microscope or Leica TCS SP MP Inverted Confocal Microscope. Cellular fluorescent intensity distribution was determined with Becton Dickinson FACScan Analytic Flow Cytometer. A 488 nm argon laser was used as the excitation light. Mass spectra were acquired with an Applied Biosystem Voyager-DE-STR MALDI-TOF mass spectrometer.

Preparation of EGFP and TAT-EGFP

Sequences of His-tagged EGFP and TAT-EGFP fusion proteins were designed according to those previously reported (Caron et al., *Mol. Ther.*, vol. 3, pp. 310-318, 2001). Fusion proteins were expressed in transformed *Escherichia coli* BL21 and purified using Nickel-resin affinity column (Sigma aldrich). EGFP and TAT-EGFP were directly used for following experiments without further processing of His-tag peptide. The concentration of EGFP was determined by an extinction coefficient of 53,000 $M^{-1}$ $cm^{-1}$ at 489 nm.

Preparation of Antennapedia Peptide EGFP Conjugate

EGFP was dissolved at a concentration of 2 mg/mL in 50 mM sodium phosphate, 0.15M NaCl, pH 7.2. 25 µL of the N-succinimidyl 3-(2-pyridyldithio) propionate (SPDP) from Sigma-aldrich at a concentration of 2 mM in DMSO was added to 1 mL EGFP solution. Mix and react for 30 min at room temperature. Purify the modified EGFP from reaction by-product and unmodified EGFP by gel filtration using 50 mM sodium phosphate, 0.15M NaCl, 10 mM EDTA, pH 7.2. Add 0.5 mg of the sulfhydryl-containing Cys(Npys) antennapedia peptide from AnaSpec, Inc. to form Antennapedia peptide EGFP conjugate and purify the final conjugate by gel filtration. MALDI-MS gave the ratio of antennapedia peptide to EGFP is about 1:1.

Protein Concentration Assay

The protein content in the form of nanocapsules was determined by bicinchoninic acid (BCA) colorimetric protein assay. Briefly, a tertrate buffer (pH 11.25) containing 25 mM BCA, 3.2 mM $CuSO_4$, and appropriately diluted protein/nanocapsules was incubated at 60° C. for 30 min. After the solution was cooled to room temperature, absorbance reading at 562 nm was determined with a UV-Vis spectrometer. BSA solutions with known concentrations were used as standards.

Apoptosis Assay

Apoptosis was detected in isolated HeLa cells using a commercially available APO-BrdU Terminal Deoxynucleotidyl Transferase dUTP Nick End Labeling (TUNEL) assay kit. Briefly, cells were seeded onto six-well plates at a density of 100,000 cells per well and cultivated in 2 mL of Dulbecco's Modified Eagle's Medium (DMEM) with 10% bovine growth serum (BGS). The plates were then incubated in 5% CO2 at 37° C. for 12 h to reach 70-80% confluency before the addition of protein/nanocapsules. After 24 h incubation, cells were first fixed with 1% paraformaldehyde in phosphate-buffered saline, pH 7.4, followed by treatment with 70% ethanol on ice. The cells were then loaded with DNA labeling solution containing terminal deoxynucleotidyl transferase and bromodeoxyuridine (BrdUrd). Cells were then stained with Alexa Fluor® 488 dye-labeled anti-BrdUrd antibody. The cells were finally stained with propidium iodide (PI) solution containing RNase A and visualized under a fluorescence microscope (Zeiss, Observer Z1) using appropriate filters for Alexa Fluor 488 and PI.

Example 1

Nanocapsule Synthesis

EGFP Nanocapsules with Degradable or Non-Degradable Crosslinkers

As illustrated in FIG. 1, polymerizable vinyl groups are covalently linked to the protein (I). Subsequent polymerization in an aqueous solution containing monomers (1, 2) and crosslinker (3 or 4) results in each protein core being wrapped in a thin polymer shell. This scheme enables the synthesis of protein nanocapsules with a non-degradable (II) or degradable (III) skin by using non-degradable (3) or degradable (4) crosslinkers, respectively. Hereinafter, the non-degradable and degradable nanocapsules are denoted nProtein and de-nProtein, respectively, where the prefix 'n' denotes 'nanocapsule'. Appropriate choice of the monomer, such as the cationic (2) or neutral (1) monomers, allows precise control of surface charge. The protein cores can be chosen from a vast library of proteins.

Protein Modification

A volume of 10 mg EGFP in 3.8 ml of pH 8.5, 50 mM sodium carbonate buffer was reacted with 4 mg N-acryloxysuccinimide in 40 ml dimethyl sulphoxide (DMSO) for 2 h at room temperature. Finally, the reaction solution was thoroughly dialysed against pH 7.0, 20 mM phosphate buffer.

Figure 2:
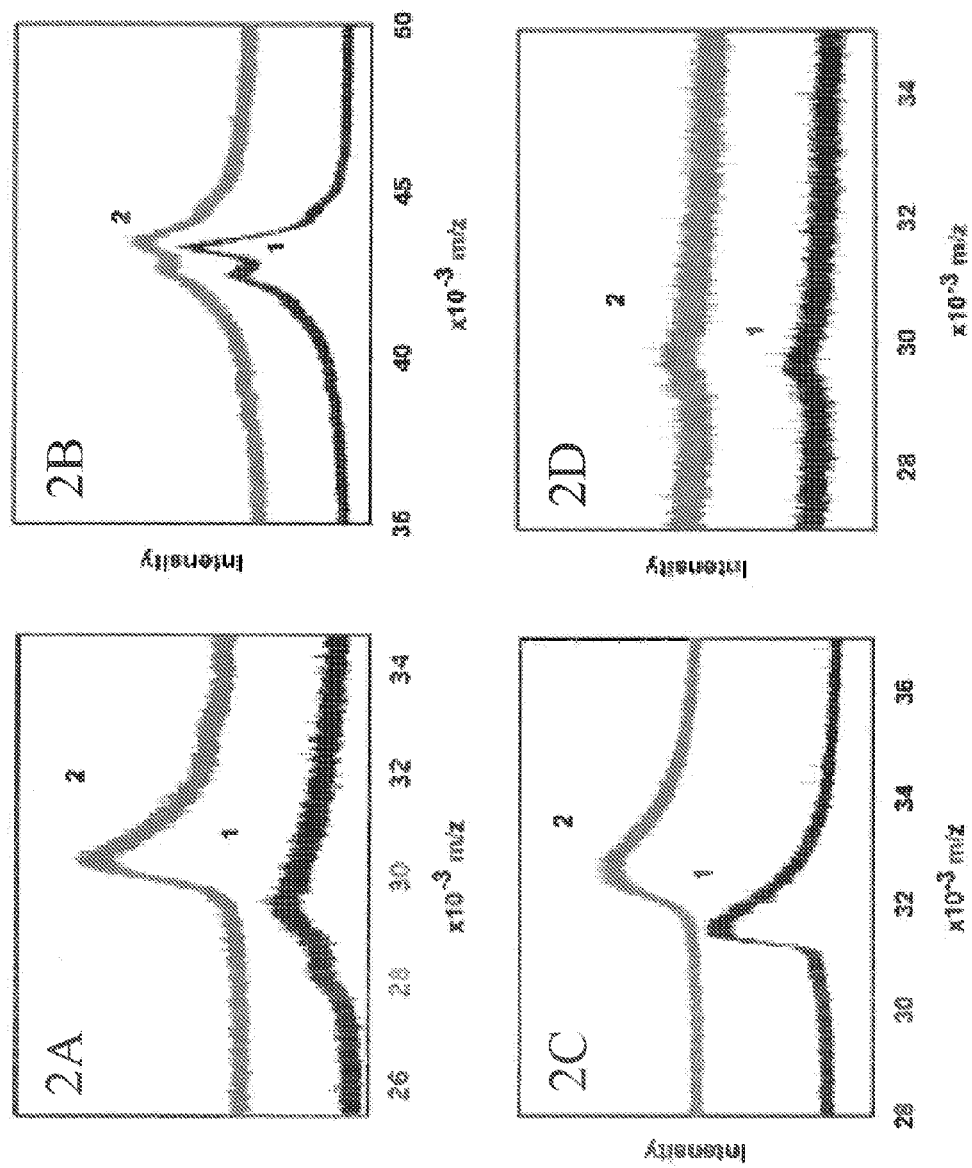
FIG. 2 shows MALDI-TOF mass spectra of proteins before and after modification with N-acryloxysuccinimide (NAS)

The degrees of modification were measured using matrix-assisted laser desorption/ionization-time of flight (MALDITOF) mass spectra, which were varied from 5 to 20 vinyl groups per protein (FIG. 2, Table 3).

TABLE 3

Molecular weight of proteins before and after modification with N-acryloxysuccinimide (measured with MALDI-TOF mass spectrometer)

| Name | Molecular Weight (MALDI-TOF MS) | Mole Ratio (Reagent to protein) | Molecular weight increase | Number of vinyl groups | Residual activity (%) |
|---|---|---|---|---|---|
| Native EGFP | 29422 | | | | |
| EGFP modified with N-acryloxysuccinimide | 30352 | 300 | 930 | 17.2 | |
| Native HRP | 43248 | | | | 100 |
| HRP modified with N-acryloxysuccinimide | 43512 | 50 | 264 | 4.9 | 98 |
| SOD | 31469 | | | | 100 |
| SOD modified with N-acryloxysuccinimide | 32543 | 100 | 1073 | 8.6 | 90 |
| Native caspase 3* | 59128 | | | | 100 |
| Caspase 3 modified with N-acryloxysuccinimide* | 59650 | 100 | 522 | 9.8 | 91 |

*Caspase-3 is a dimer; molecular weights were calculated by doubling mass readings.

Nanocapsule Polymerization

Figure 3:
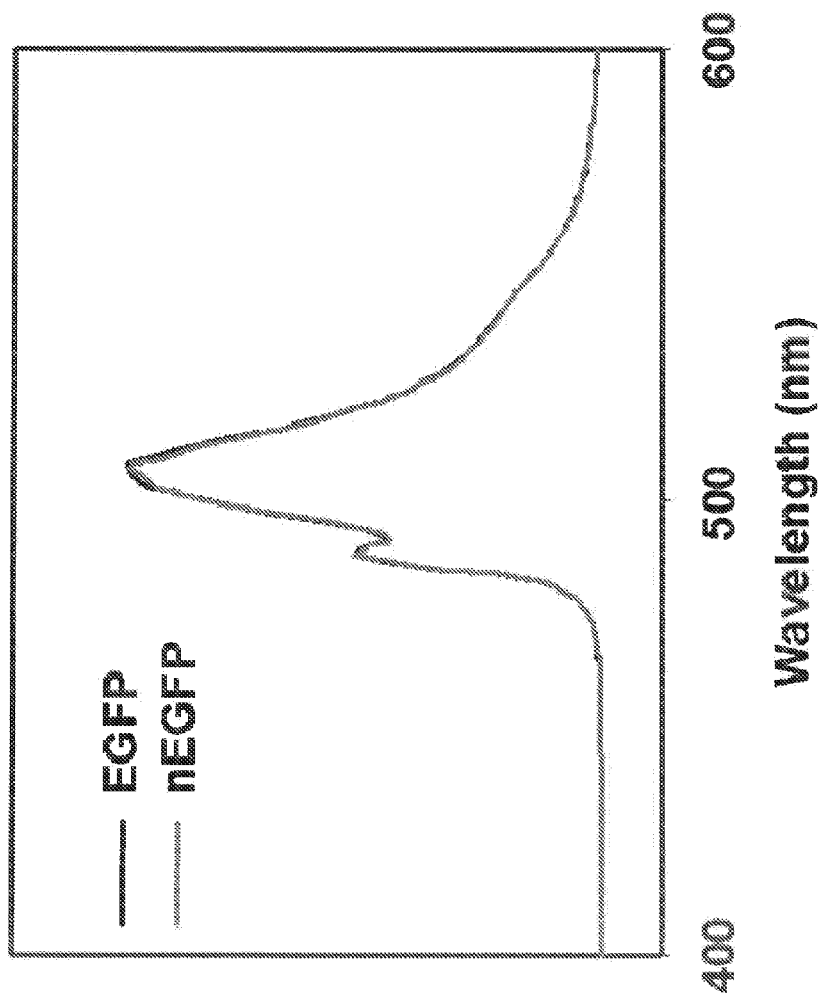
FIG. 3 shows the fluorescence spectra of native EGFP and nEGFP in 50 mM pH 7.0 phosphate buffer using an excitation wavelength of 489 nm.

Using 5 ml acryloylated EGFP solution at 1 mg ml$^{-1}$, radical polymerization from the surface of the acryloylated protein was initiated by adding 2 mg ammonium persulphate dissolved in 30 ml deoxygenated and deionized water and 4 ml N,N,N',N'-tetramethylethylenediamine into the test tube. A specific amount of 2-dimethylaminoethyl methacrylate, acrylamide and N,N'-methylene bisacrylamide (non-degradable crosslinker) or glycerol dimethacrylate (degradable crosslinker) (molar ratio=5:5:1) dissolved in 0.5 ml deoxygenated and deionized water was added to the test tube over 60 min. The reaction was allowed to proceed for another 60 min in a nitrogen atmosphere. Finally, dialysis was used to remove monomers and initiators. As-synthesized EGFP nanocapsules show similar fluorescent spectra to those of native EGFP (FIG. 3). The yield of the protein nanocapsules was higher than 95%. The unmodified EGFP was removed using size exclusion chromatography.

HRP Nanocapsules

To synthesize HRP nanocapsules, 4-dimethylaminoantipyrine (1:10 weight ratio to HRP) was added into the reaction mixture as a stabilizer during acryloylation and polymerization. Similar acryloylating, polymerization, and purification processes were conducted to synthesize the HRP nanocapsules.

SOD, CAS, BSA, HRP Nanocapsules

SOD, CAS, HRP, NIR-667-labelled-BSA and rhodamine-B labelled-HRP nanocapsules were synthesized using methods similar to that of EGFP nanocapsules. NIR-667-labelled BSA and rhodamine-B-labelled HRP were synthesized by modifying the proteins using a conjugating technique. CAS was expressed and purified using a method similar to that of EGFP; the plasmid used, pHC332, was a generous gift from Dr A. Clay Clark (North Carolina State University). Cu, Zn-SOD from bovine erythrocytes and horseradish peroxidase (Sigma-Aldrich) were used after dialysis against 20 mM pH 7.0 phosphate buffer.

Au-Nanoparticle-Labeled Nanocapsules

Au-nanoparticles (Mono-sulfo-N-hydroxy-succinimido nanogold from Nanoprobe, N.Y.) were reacted with native HRP at 5:1 molar ratio in buffer solution at pH 7.5 for 1 hr. Gel filtration (Superdex-75) was used to remove the excessive nanogold. Molar concentrations of the nanogold and protein were calculated from the UV/vis spectrum based on the molar extinction coefficient of 155,000 $M^{-1}cm^{-1}$ for the nanogold at 420 nm. The resulting Au-labeled nanocapsules contain a gold/HRP ratio of 0.94. Labeled HRP was then used to synthesize the nanocapsules using the similar protocol. For better imaging in TEM, a silver enhancement technique was used. Briefly, the Au-labeled nanocapsules was dropped onto a TEM grid and rinsed with deionized water. Then the grid was floated on a freshly prepared Ag-containing developer for 1-2 minutes, rinsed with water, and stained using 1% sodium phosphotungstate at pH 7.0. This process resulted in the formation of uniformed nanoparticles with 3-4 nm in diameter.

Nanocapsule Characterization

Figure 4:
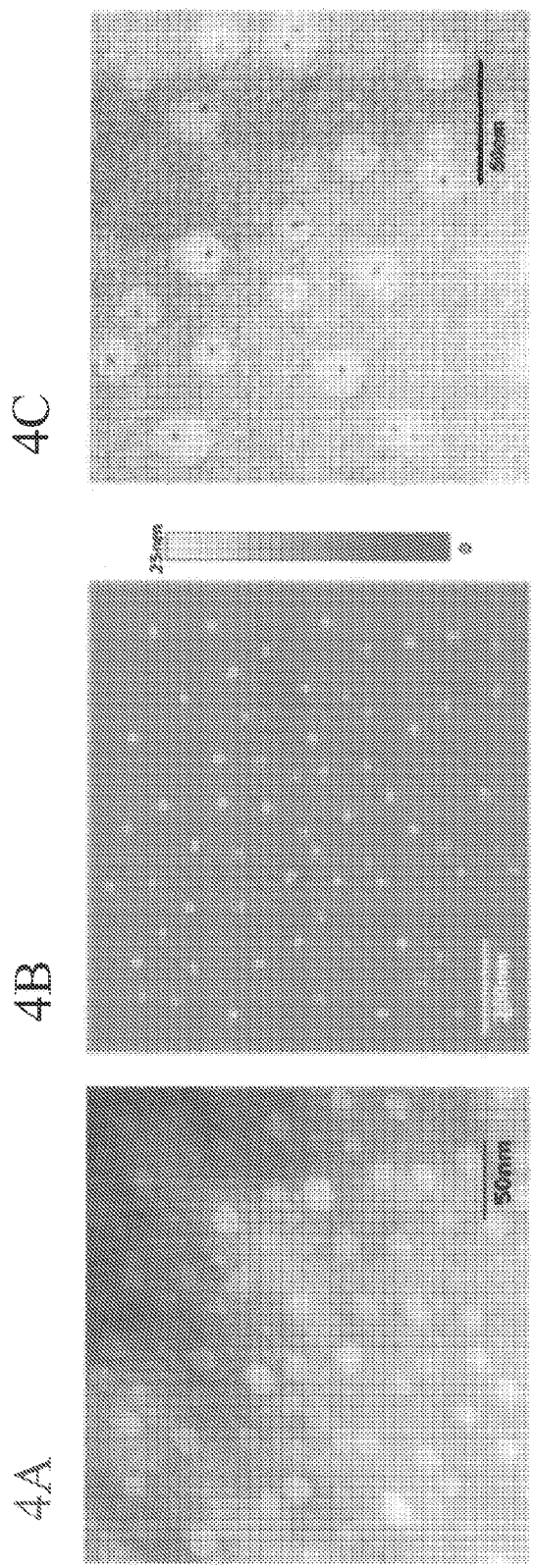
FIG. 4 shows the sizes of exemplary nanocapsules.
Figure 5:
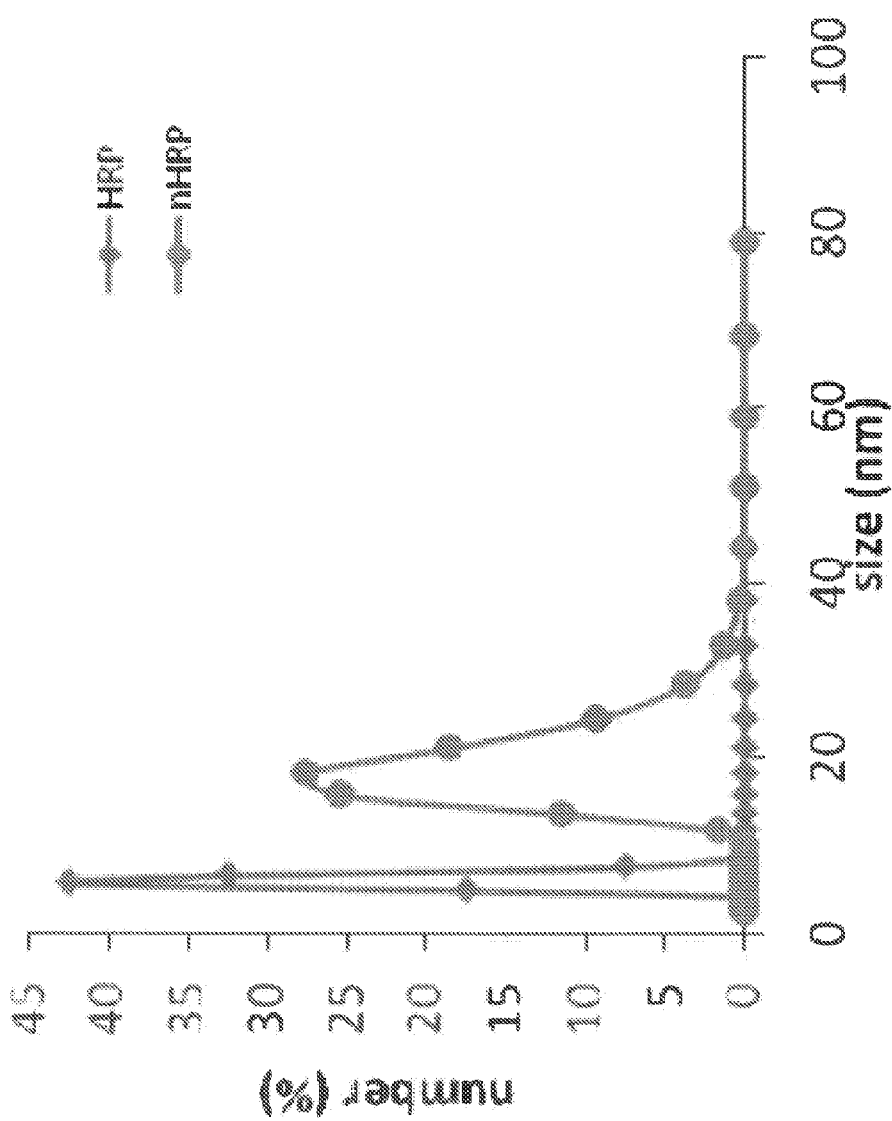
FIG. 5 shows the size distribution of HRP and nHRP determined with dynamic light scattering (DLS).

FIGS. 4A and 4B are representative TEM and AFM images of the HRP nanocapsules showing a uniform diameter of c.a. 15 nm. Dynamic light scattering (DLS) suggested the HRP nanocapsules exhibit a narrow size distribution at 16.8 nm (FIG. 5). The larger diameter determined by the DLS could be attributed to the hydration layer in aqueous solution. Since the hydrodynamic radius of HRP molecule is around 5 nm, the average shell thickness is approximately 5 to 8 nm. By labeling each HRP enzyme with a single 1.4 nm gold nanoparticle, it was observed that most nanocapsules only contain a single gold nanoparticle (FIG. 4C), further confirming a single-protein core-shell structure. Moreover, tuning the weight ratio of DMAEMA (positive charged) to AAm (neutral) from 0:1, 1:3 and 1:1 allows the synthesis of BSA nanocapsules with adjustable zeta potentials from −12.8, 8.64 to 15.2 mV (FIG. 6), respectively. This simple method provides an effective route to the preparation of novel protein-intracellular-delivery vectors with well-controlled size, surface charge and protein core.

Example 2

Nanocapsule Protein Activity

Relative catalytic activity of the native HRP (Left) and the HRP nanocapsules (Right) was determined. The activity testing of the native HRP and HRP nanocapsules was followed the exiting protocol (Davis et al., *J. Biol. Chem.*, vol. 256, pp. 5992-5996, 1981). Briefly, During a run, 0.9 ml of pH 5.5, 100 mM phosphate citrate, 0.05 ml of 0.02 M $H_2O_2$, and 10 µL of 0.2 µg/mL HRP or HRP nanocapsules were added into a test tube. The reaction was initiated by adding 0.05 ml of DMSO containing 0.02 M TMB and monitored at 655 nm. The oxidation rates of the TMB were interpreted from the slopes of the initial linear parts of the adsorption curves using a molar absorption coefficient (39,000 $M^{-1}$ $cm^{-1}$) for the oxidation product of TMB.

Example 3

Stability to Proteases

EGFP and EGFP nanocapsules were incubated with both of trypsin and α-chymotrypsin at 1 mg/mL at 50° C. in PBS buffer. Fluorescent intensity of the EGFP and EGFP nanocapsules was determined at different time intervals with an excitation wavelength at 489 nm.

Figure 8:
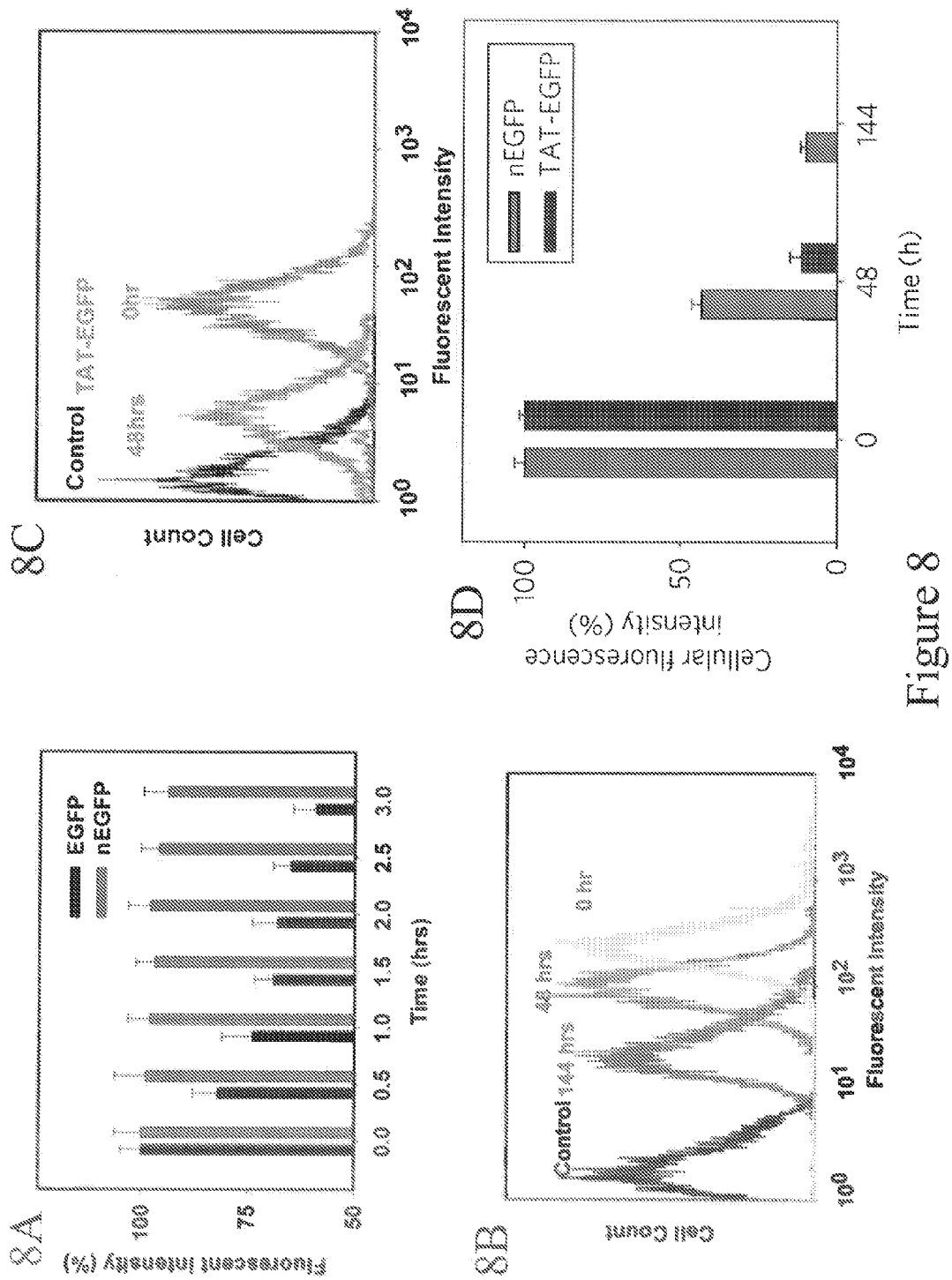
FIG. 8 shows the stability of exemplary nanocapsules to proteases.

Poor protein stability due to the wide presence of proteases in physiological environment is another challenge for applications of therapeutic proteins. The fluorophore inside the EGFP molecule, which is formed through the posttranslational cyclization of the tripeptide Ser65-Tyr66-Gly67, is extremely sensitive to the surrounding microenvironment (Tsien, R. Y., *Annu. Rev. Biochem.*, vol. 67, pp. 509-544, 1998). Without protection of the outside β-barrel structure, the fluorophore can be easily destroyed and quenched (Ormo et al., *Science*, vol. 273, pp. 1392-1395, 1996). The presence of the polymer shell protects the protein core from proteolysis. FIG. 8A compares the fluorescence intensities of the native EGFP and the EGFP nanocapsules after exposure to 1 mg/mL protease (trypsin and α-chymotrypsin) at 50° C. for 3 hrs. The native EGFP only kept 60% of its original fluorescence intensity whereas the nanocapsules retained more that 90%.

To further confirm the stability of the nanocapsules cellular fluorescence intensity after the transduction of the nanocapsules was monitored. FIG. 8B shows fluorescent intensity distribution of HeLa cells at 0, 48, and 144 hrs after transduction. Inevitably, fluorescent intensity of the HeLa cells decreases with time as a result of cell propagation. Nevertheless, fluorescence intensity of the cells transducted with the EGFP nanocapsules is significantly higher than the control (native EGFP) even after 144 hrs. Consistently, although the TAT-EGFP is being considered as an approach with good delivery efficiency, similar to other proteins, they are subjective to the protease attack. Compared with 91% lost in the cellular fluorescent intensity 48 hours after incubation with the TAT-EGFP, only 42% decrease was observed for the EGFP nanocapsules (FIG. 8D).

Example 4

Cellular Internalization

Cellular internalization studies were assessed via fluorescence microscopic technique and fluorescence-activated cell sorting (FACS). HeLa cells were cultured in Dulbecco's modified Eagle's medium (DMEM) supplemented with 10% bovine growth serum (BGS) and 1% penicillin/streptomycin. Cells (20000 cells/well, 24-well plate) were seeded the day before adding the nanocapsules. Nanocapsules or native proteins with different concentrations were added into the cell medium. After incubation at 37° C. for 2 to 4 hrs, the cells were washed three times with PBS and either visualized with a fluorescent microscope or trypsinized, centrifuged, and re-suspended in PBS and analyzed via FACS. The endosome/ lysosome staining was performed according to manufacture's manual. Briefly, after incubation with rhodamine-labeled HRP nanocapsules, cells were briefly washed, fixed with 2% formaldehyde, permeated with PBS/1% Triton, blocked with 5% BSA and treated with rabbit anti-EEA antibody (for early endosome) or rabbit anti-Rab7 antibody (for lysosome) overnight. Cells were stained with Alexa488 goat anti-rabbit IgG and then observed with confocal microscope.

Figure 9:
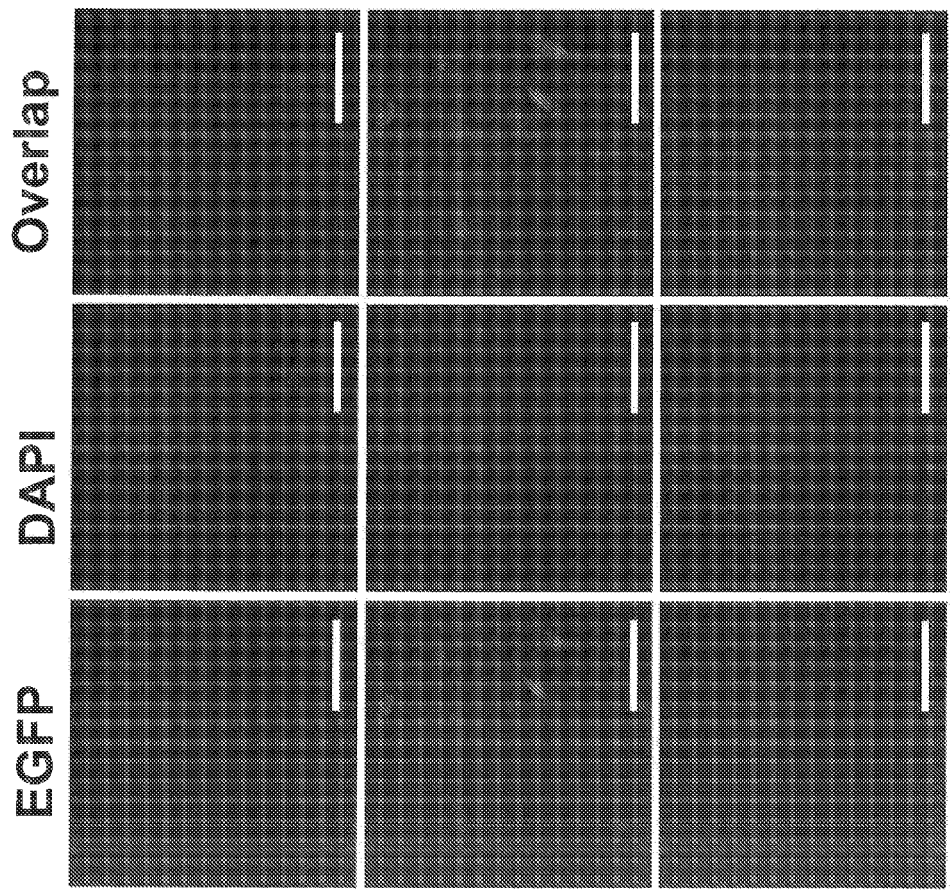
FIG. 9 shows fluorescent microscope images of HeLa cells after 3-hour incubation with EGFP nanocapsules or untouched EGFP at defined temperatures, cells were counter-stained with DAPI, (scale bar=50 µm).
Figure 10:
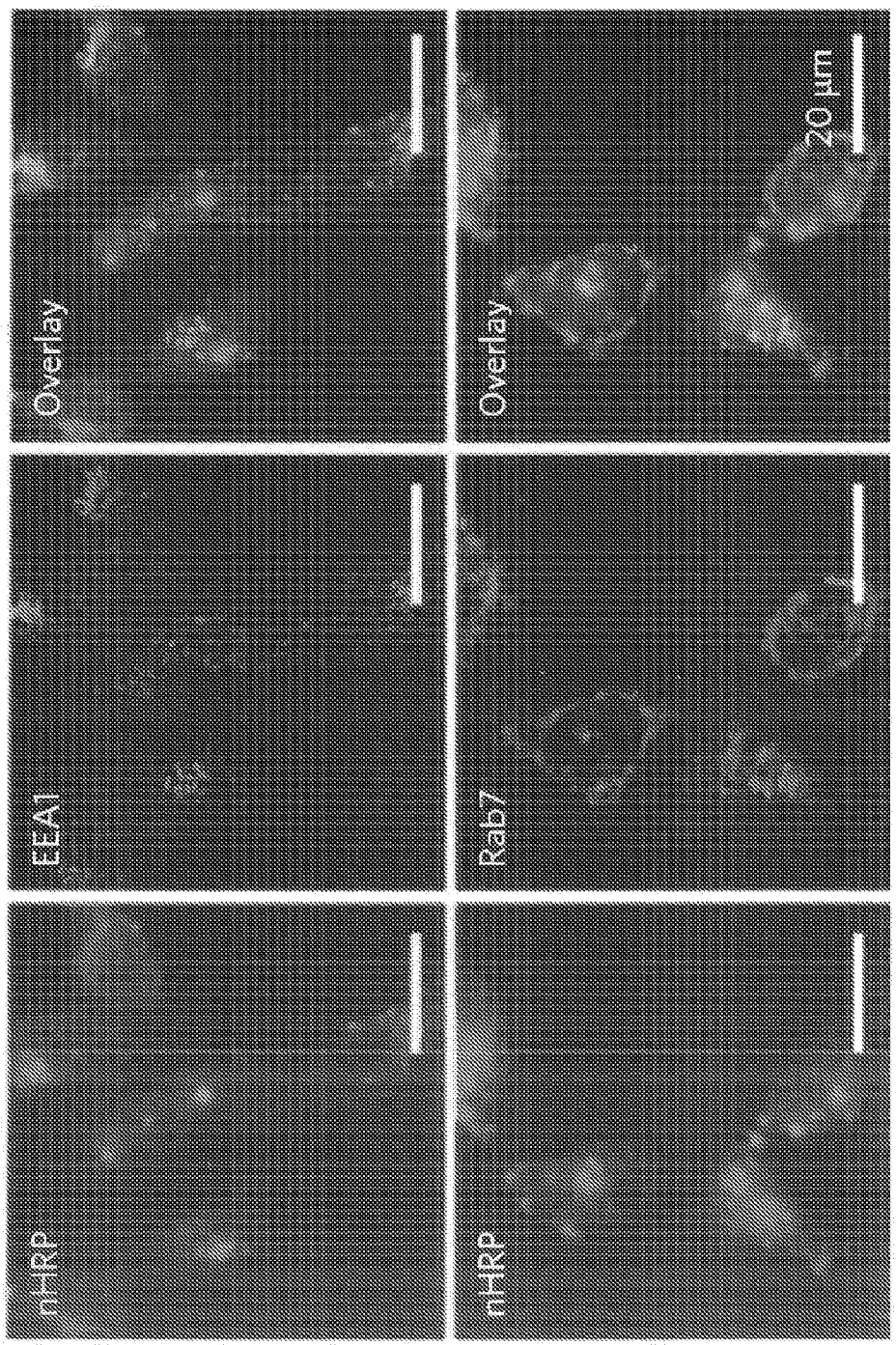
FIG. 10 shows fluorescent images showing the uptake of rhodamine-labelled nHRP. Cells were counter-stained with EEA1 (for early endosomes) or Rab7 (for lysosomes).
Figure 11:
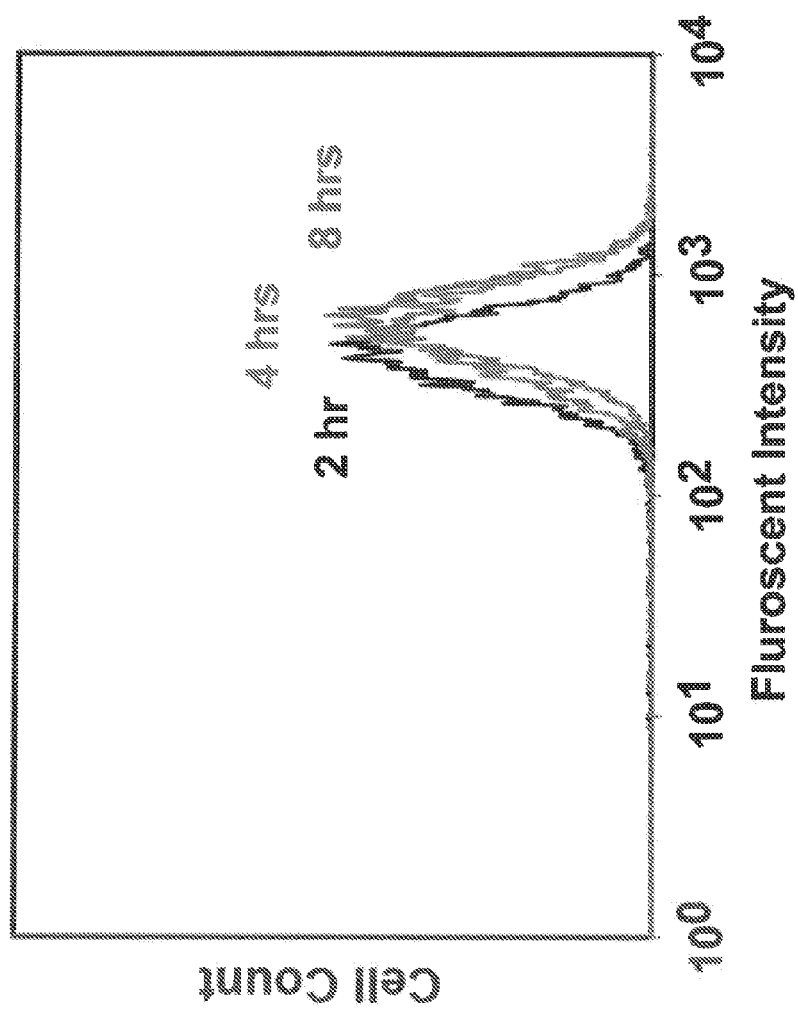
FIG. 11 shows Hela cell fluorescence intensity after incubation with EGFP nanocapsules with different time. HeLa cells were incubated with 400 nM EGFP nanocapsules for different time, washed, trypsinized and subjected to FACS analysis.
Figure 12:
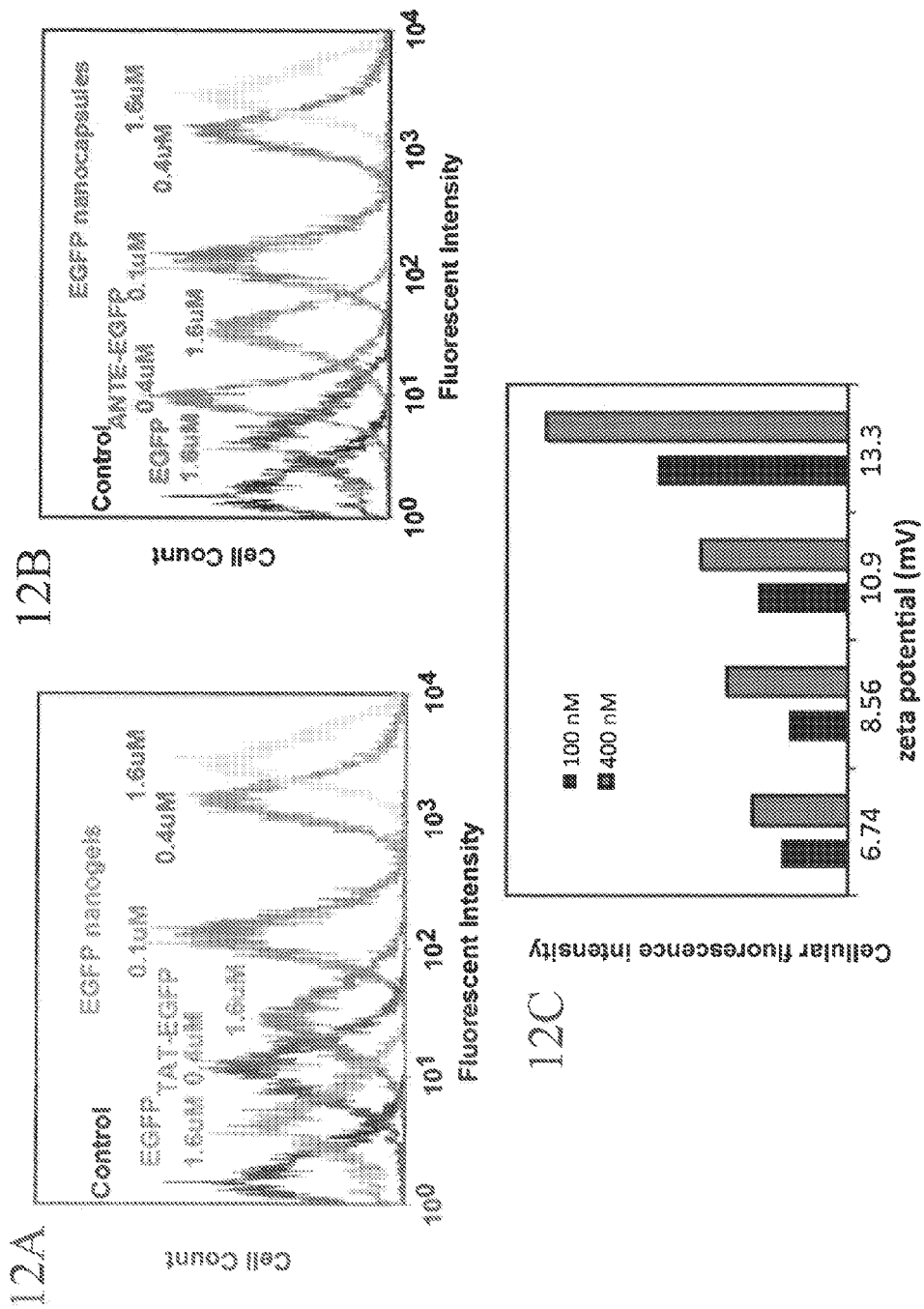
FIG. 12 shows nanocapsules compared with TAT-EGFP and antennapedia-EGFP conjugates, and the effect of zeta potential on cellular uptake.

Cell transduction was studied using the EGFP nanocapsules as a model. FIG. 9 shows the fluorescence microscope images of HeLa cells after 2-hour co-culture with 400 nM EGFP nanocapsules or unmodified EGFP. Compared with the unmodified EGFP, nanocapsules are more effectively internalized by HeLa cells. Extending the incubation time from 2 hours to 4 or 8 hours gave slightly increased fluorescence intensity from 448 to 559 or 619, respectively, indicating the uptake mostly finished within 2 hrs (FIG. 11). The intensity of cellular fluorescence increased at higher nanocapsule concentrations (FIG. 12A). As a comparison, the cells incubated with TAT-EGFP fusion protein (TAT is a cell-penetrating peptide derived from HIV virus) for 2 hours showed 100 times less fluorescence intensity than that of the nanocapsule-treated cells (FIG. 12A). Additionally, effect of surface charge of the nanocapsules on cellular uptake efficiency was also investigated. It was found that the HeLa cells incubated with 400 nM nanocapsules with zeta potential of 13.3 mV had an average fluorescence intensity of 398, which is 3.2 times as much as that obtained with 6.7 mV nanocapsules (FIG. 12C).

Figure 13:
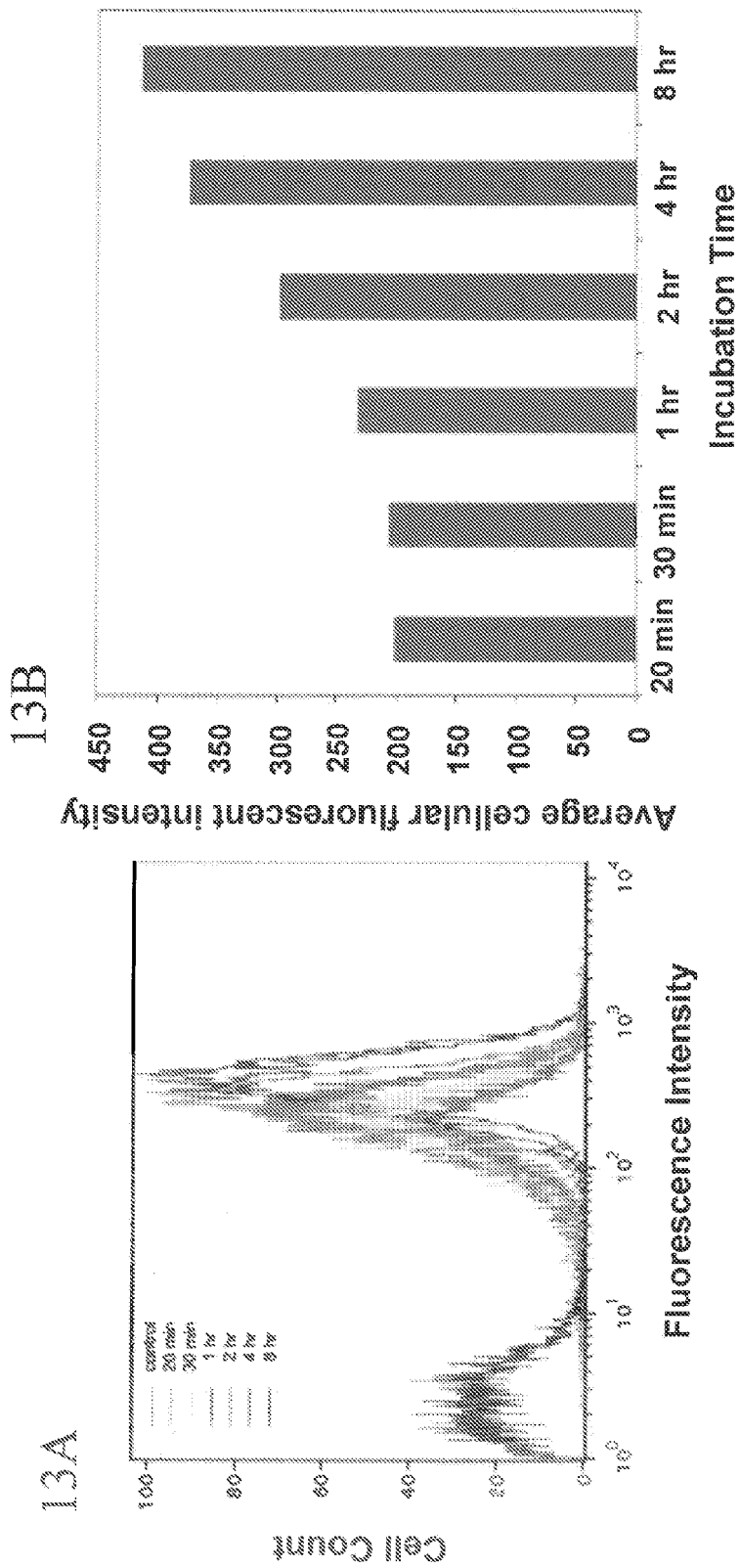
FIG. 13 shows the effect of extended incubation time on nanocapsule uptake.
Figure 14:
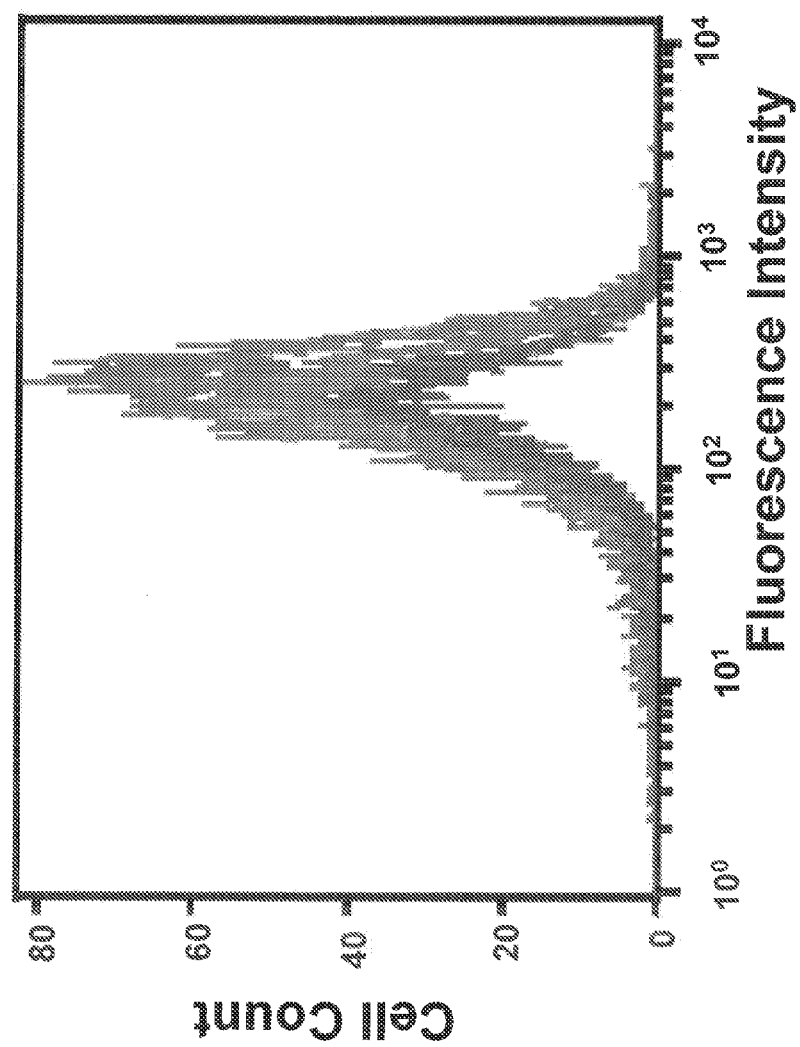
FIG. 14 shows the effect of nanocapsule size on cellular uptake. Cellular fluorescent intensity distribution of HeLa cells after incubation with nEGFP with different sizes (red: 7.53 nm, green: 10.6 nm, purple: 15.7 nm).

Cells carrying nEGFP show significantly higher fluorescence intensity than those with native EGFP (FIG. 12A). Compared with CPP-assisted delivery, this strategy is advantageous. At the same protein concentration, cells incubated with nanocapsules show two to three orders of magnitude higher fluorescence intensities than those with TAT-EGFP fusion proteins (FIG. 12A) or antennapedia-EGFP conjugates (FIG. 12B; TAT and antennapedia are CPPs derived from HIV-Tat protein and antennapedia homeodomain, respectively). It was found that uptake of nanocapsules increased with time (FIG. 13), concentration (FIG. 12A) and zeta potential (FIG. 12C); however, no significant impact of nanocapsule size (in the range 7.5-15.7 nm, FIG. 14) was observed.

Endocytosis Inhibition

The uptake pathway of the nanocapsules may involve an endocytosis process. Incubating HeLa cells with the EGFP nanocapsules at 4° C. for 3 hrs showed a much lower cellular uptake than that at 37° C. (FIG. 9). This observation confirms that the cellular uptake was mainly through an activated pathway, i.e. endocytosis, which is consistent with the endocytosis process observed with most cationic CPPs and polymers (Brooks et al., *Adv. Drug Deliv. Rev.*, vol. 57, pp. 559-577, 2005; Poon et al., *Biochem. Soc. Trans.*, vol. 35, pp. 778-793, 2007; Futami et al., *J. Biosci. Bioeng.*, vol. 99, pp. 95-103, 2005; Fischer et al., *J. Bio. Chem.*, vol. 279, pp. 12625-12635, 2004).

Figure 15:
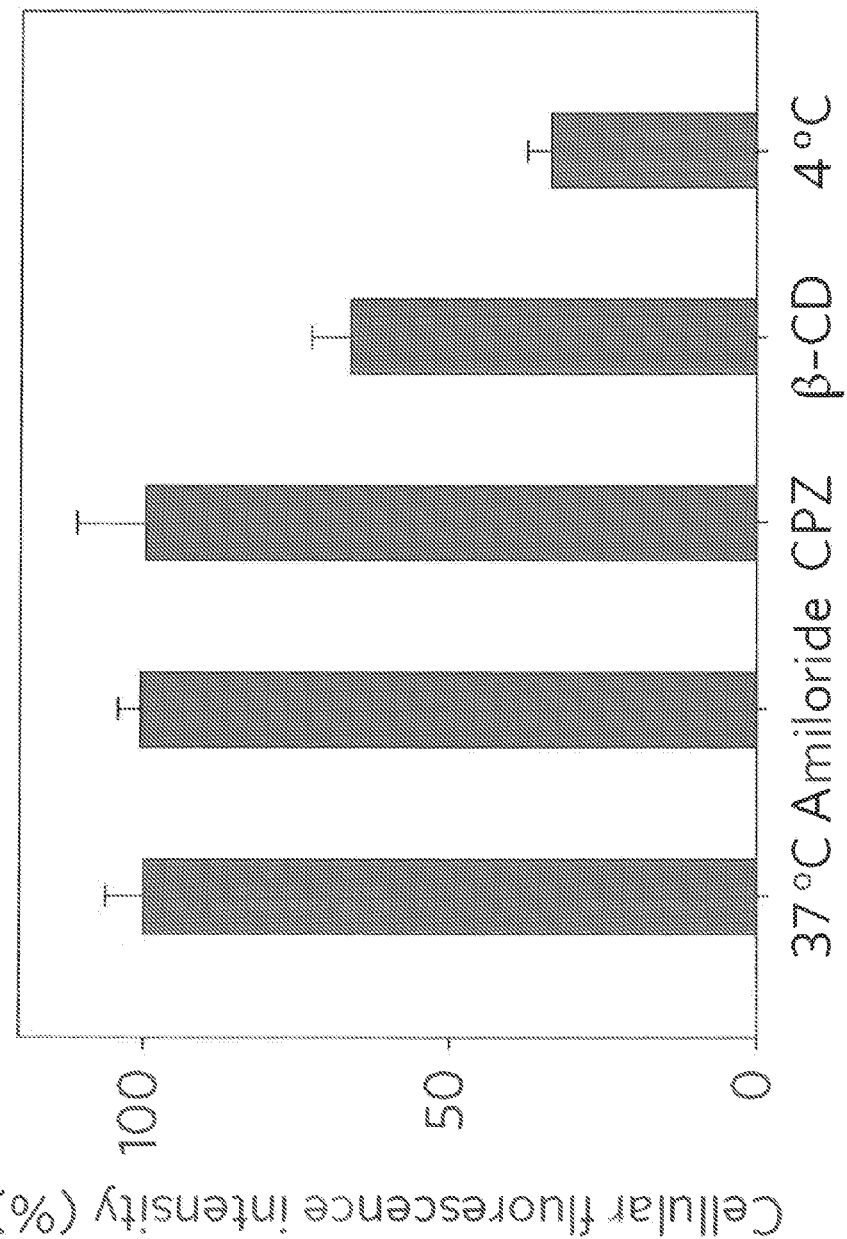
FIG. 15 shows average cellular fluorescence intensity of HeLa cells at different temperatures and in the presence of three different endocytosis inhibitors: Amiloride, CPZ and β-cyclodextrin (β-CD). Fluoresence intensity is normalized to cells incubated with nEGFP at 37° C.

HeLa cells (20000 cells/well, 24-well plate) were seeded the day before adding the nanocapsules. Before the experiment, the medium was then replaced with 0.5 ml of fresh medium with 2 mM amiloride (inhibitor for macropinocytosis), 20 μg/mL chloroproamzine (CPZ, inhibitor for clathrin-mediated endocytosis), or 5 mM β-cyclodextrin (β-CD, inhibitor for caveolae-mediated endocytosis). After 30 min, 50 nM EGFP nanocapsules were added into cell medium and incubate at 37° C. for 2 h. After washing with PBS, the cells were trypsinized, centrifuged, re-suspended in PBS and analyzed via FACS. HeLa cells incubated in medium without endocytosis inhibitors were used as control. Of three endocytosis inhibitors applied (FIG. 15), only β-cyclodextrin (β-CD) effectively inhibited nanocapsule uptake, suggesting a caveolae-mediated endocytosis pathway.

Chloroquine Treatment

Magnified fluorescence image of HeLa cells pre-incubated with the EGFP nanocapsules (FIG. 16) reveals an inhomogeneous distribution of the nanocapsules.

HeLa cells (20000 cells/well, 24-well plate) were seeded the day before adding the nanocapsules. Before the experiment, the medium was replaced with 0.5 ml of fresh medium with 100 μM chloroquine; and the cells were incubated with 0.2 μM of EGFP nanocapsules for 3 h. After washing with PBS, the cells were observed with fluorescent microscope. HeLa cells incubated in medium without chloroquine were used as control.

Figure 16:
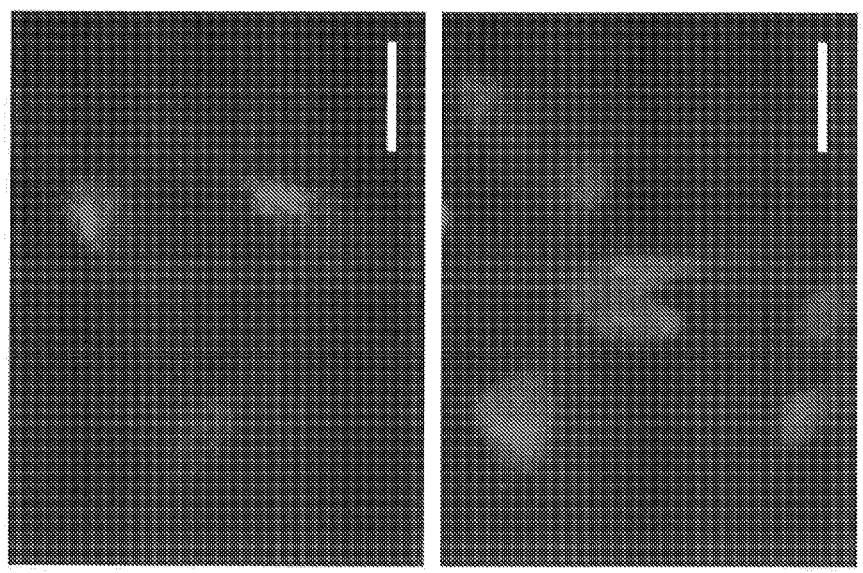
FIG. 16 shows fluorescence microscope images of HeLa cells after incubation with EGFP nanocapsules for 3 hours with or without treatment with 100 µM chloroquine (scale bar=20 µm).
Figure 17:
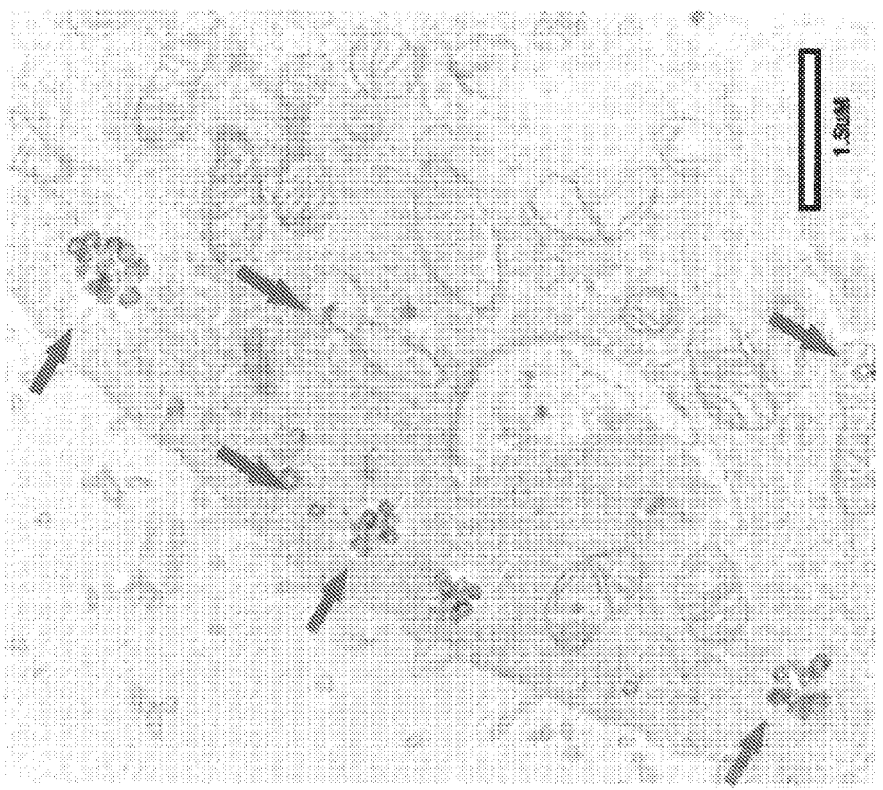
FIG. 17 shows TEM image of a HeLa cell after incubation with gold quantum-dot-labelled HRP nanocapsules. Dark arrows show dispersion of single nanocapsules in the cell cytosol; light arrows show clusters of nanocapsules.

Chloroquine, a lysosomotropic agent (Fischer et al., *J. Bio. Chem.*, vol. 279, pp. 12625-12635, 2004; Ciftci et al., *Int. J. Pharm.*, vol. 218, pp. 81-92, 2001), was introduced to the medium during incubation to destruct the endosomes. As a result, the number of nanocapsules entrapped in the vesicles was reduced, resulting in uniform dispersion of the nanocapsules within the cells (FIG. 16). Nevertheless, prior to the use of chloroquine, high-concentration nanocapsules were observed within the cytosol (Red arrow in FIG. 17), suggesting a partial release of the nanocapsules from the endosomes possibly via the "proton-sponge" effect (Akinc et al., *J. Gene Med.*, vol. 7, pp. 657-663, 2004).

TEM Study

HeLa cells transducted with nanogold-labeled nanocapsules were fixed with 1% glutaraldehyde for 1 hr at 4° C., treated with 2% osmium tetroxide for 1 hr, and dehydrated in a graded series of ethanol washes. The treated cells were then embedded in Epon 812 (Electron Microscopy Sciences, Fort Washington, Pa.). Ultrathin (~80 nm) sections were stained with 2% uranyl acetate and examined using TEM.

Consistently, TEM image of HeLa cells pre-incubated with the gold-labeled nanocapsules shows aggregated gold particles with a contour similar to that of endosomes (FIG. 17, green arrow), suggesting the entrapping of the nanocapsules within the endosomes.

Multiple Protein Internalization

Figure 18:
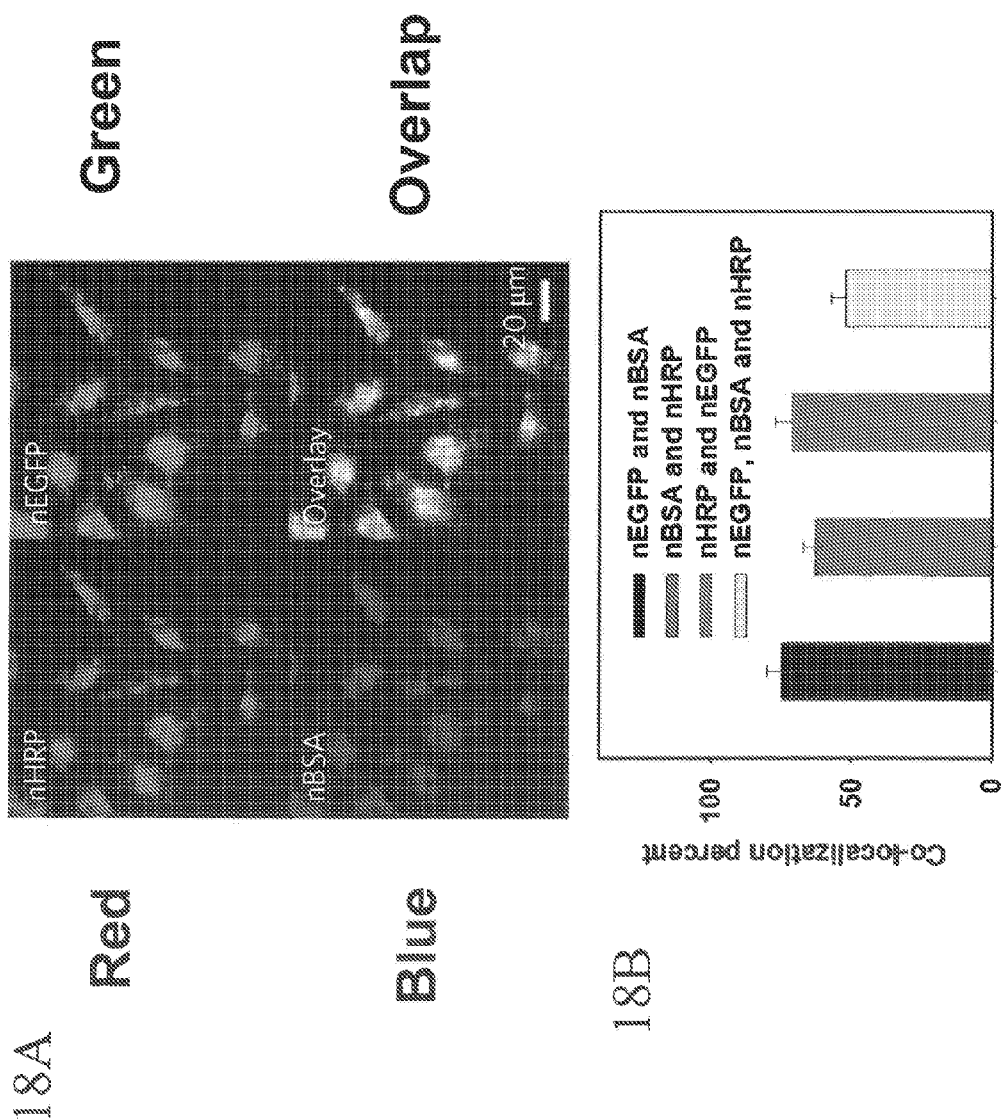
FIG. 18 illustrates multiple protein delivery.

This method can be generalized to multiple-protein delivery with low toxicity. FIG. 18A shows florescence images of HeLa cells simultaneously internalizing nanocapsules of EGFP (green), rhodamine-B-labeled HRP (red) and AlexaFluoro-664-labeled BSA (blue). Quantification of co-localization after simultaneous transduction is shown in FIG. 18B. Such multiple-protein delivery holds great promise for therapies where more than one proteins act synergistically or in tandem (Yamauchi et al., *Japan. J. Cancer Res.*, vol. 83, pp. 540-545, 1992; Kaliberov et al., *Cancer Gene Ther.*, vol. 13, pp. 203-214, 2006).

Example 5

In Vitro Activity

Cell Viability

The toxicity of the nanocapsules was assessed by the MTT assay using native proteins as control. HeLa cells (7000 cells/well) were seeded on a 96-well plate the day before exposure to the nanocapsules. Nanocapsules with different concentrations were incubated with the cells for 2-4 hrs, removed from the mixture, and incubated with fresh media for 24 hrs. The MTT solution (20 μL) was added to each well and incubated for 3 h. The medium was then removed and 100 μL DMSO was added onto the cells. The plate was placed on a shaking table, 150 rpm for 5 min to thoroughly mix the solution, and then absorbance readings were measured at 560 nm. Untreated cells were used as the 100% cell proliferation control.

Figure 19:
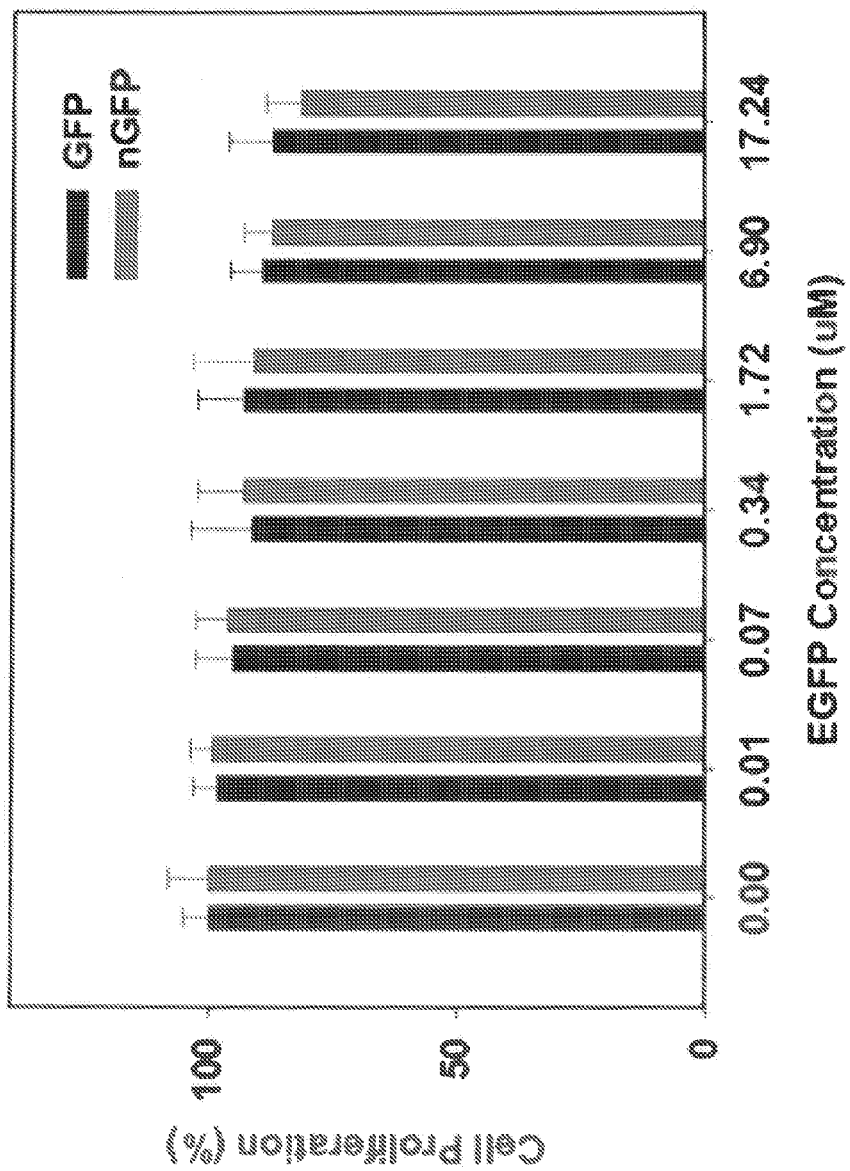
FIG. 19 shows relative cellular proliferation rate of HeLa cells after 3-hour co-culture with EGFP nanocapsules followed by incubation in fresh medium for 12 hours, determined with MTT assay, cell proliferation rates were normalized to HeLa cells without treatment of any agents.

FIG. 19 compares the viability of HeLa cells after exposure to different concentrations of EGFP nanocapsules and native EGFP. Both the EGFP nanocapsules and the native EGFP show similar cytotoxicities at each concentration tested (FIG. 19). Even under the exposure to 17.24 µM EGFP nanocapsules, the cell viability decreased by only 15%.

Cancer Cell Growth Inhibition

HeLa cells placed in 96-well plates (2000 cells/well) were incubated with HRP nanocapsules or native HRP for 4 hrs then exposed to the indole-3-acetic acid (IAA) at different concentrations for 12 hrs. The half maximal inhibitory concentration ($IC_{50}$) was determined from the HeLa cell viability curve assayed using MTT.

Figure 7:
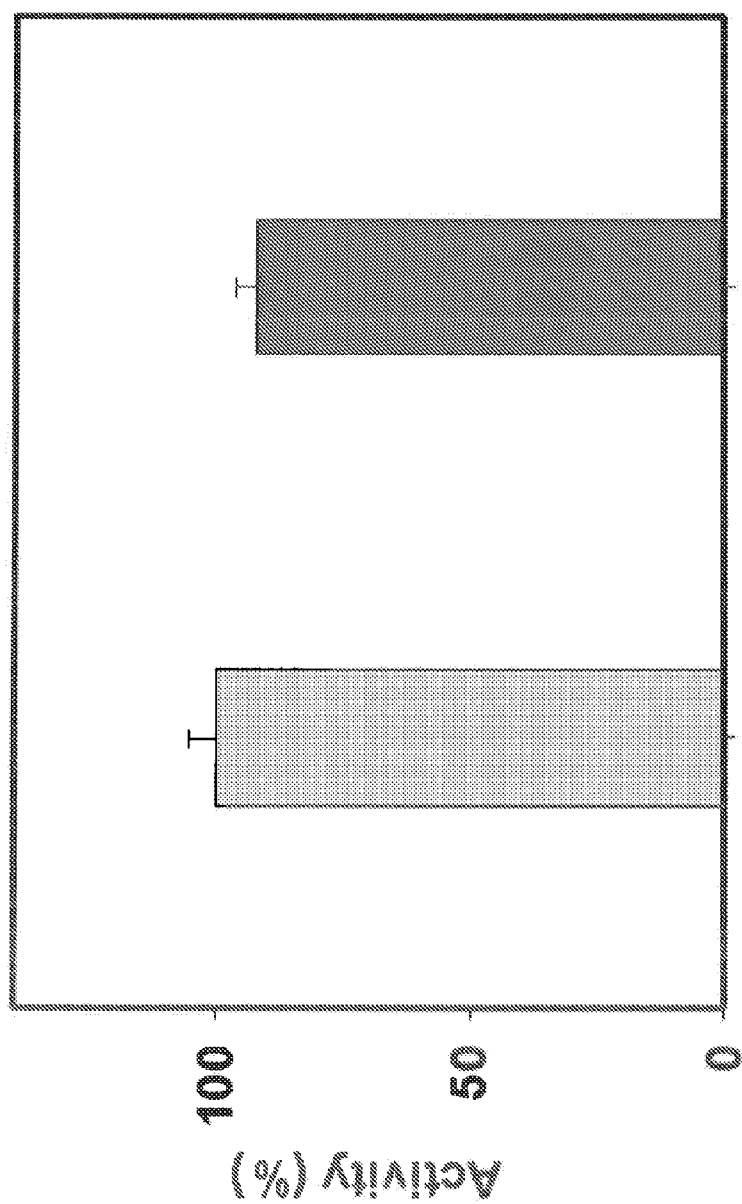
FIG. 7 shows the relative catalytic activity of the native HRP (Left) and nHRP (Right). The activity testing of the native HRP and nHRP was followed the exiting protocol (Davis et al., *J. Biol. Chem.*, vol. 256, pp. 5992-5996, 1981). Briefly, during a run, 0.9 ml of pH 5.5, 100 mM phosphate citrate, 0.05 ml of 0.02 M $H_2O_2$, and 10 µL of 0.2 µg/mL HRP or nHRP were added into a test tube. The reaction was initiated by adding 0.05 ml of DMSO containing 0.02 M TMB and monitored at 655 nm. The oxidation rates of the TMB were interpreted from the slopes of the initial linear parts of the adsorption curves using a molar absorption coefficient (39,000 M-1cm-1) for the oxidation product of TMB
Figure 20:
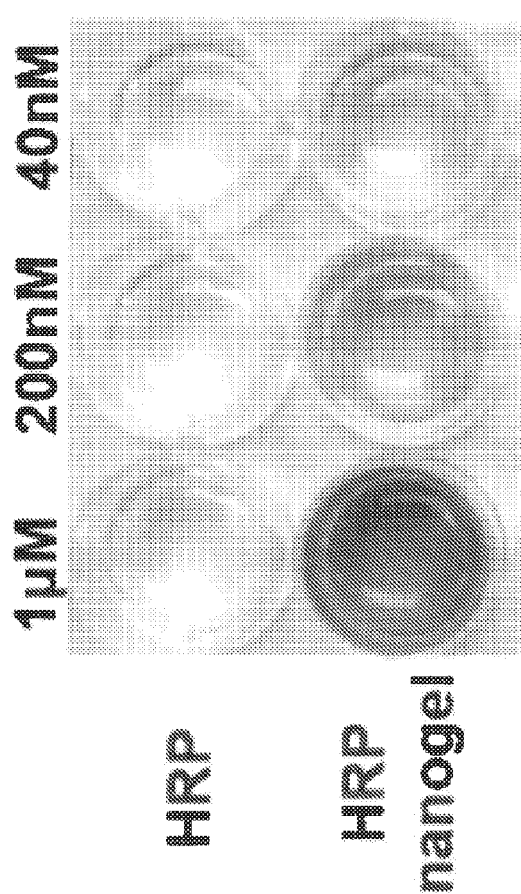
FIG. 20 shows pictures of HeLa cells after incubation with HRP or HRP nanocapsules at different concentrations for 3 hours, followed by PBS washing and incubation with 1 mM TMB (3,3',5,5'-tetramethylbenzidine) and 1 µM $H_2O_2$ in PBS for 10 min.

Besides high delivery efficiency, low toxicity, and long-term stability, the protein delivery system cannot be effective if the delivered pharmaceutical protein cannot retains its bioactivity with fully biocatalytic activity after internalization. To determine whether delivery of enzyme nanocapsules results in active intracellular enzymes, the delivery of HRP and SOD nanocapsules was investigated. The combination of indole-3-acetic acid (IAA) and HRP has recently been proposed as a potential prodrug cancer therapy (Folkes et al., *Biochem. Pharmacol.*, vol. 61, pp. 129-136, 2001). IAA is a well tolerated plant hormone in human, and could be specifically transformed to a free radical intermediate by HRP and induce apoptosis in mammalian cells (de Melo et al., *Toxicol. Lett.*, vol. 148, pp. 103-111, 2004). HRP nanocapsules were synthesized and shown to retain 92% of the native HRP activity (FIG. 7). To determine if HRP nanocapsules retained their activity after cellular internalization, HeLa cells were incubated with HRP and HRP nanocapsules and exposed to the chromogenic substrate 1 mM TMB (3,3',5,5'-tetramethylbenzidine) and 1 µM $H_2O_2$ (FIG. 20). The nanocapsule-transducted cells show green color intensifying with increasing nanocapsule concentration, confirming the successful delivery of the nanocapsules that are active within the cells. To further determine the intracellular activity of HRP nanocapsules, HeLa cells were incubated with HRP or HRP nanocapsules for 4 hours. After washing, IAA was added into medium. With increasing IAA concentration, the cells pretreated with the HRP nanocapsules showed a dramatic decrease in cell viability, whereas those with native HRP performed similarly as the control cells, (FIG. 21A), demonstrating that the enzyme presented biocatalytic activity intracellularly.

Figure 21:
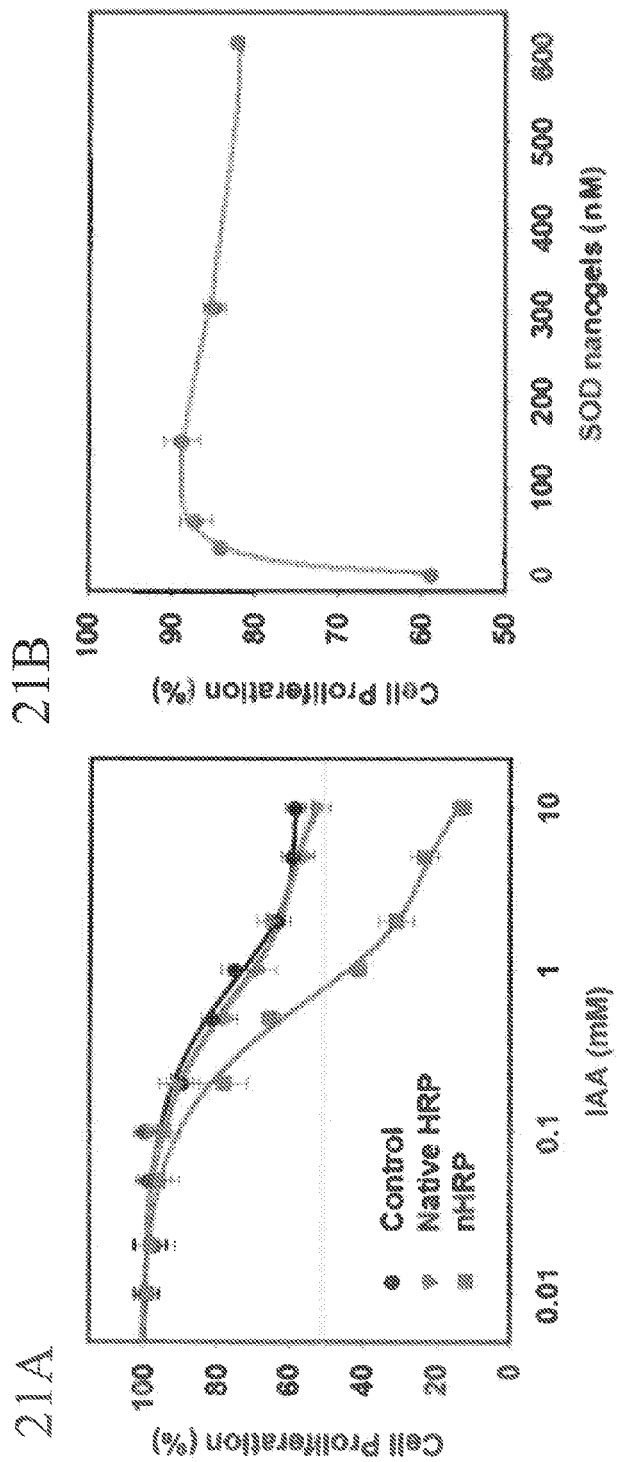
FIG. 21 shows the activity of HRP and SOD nanocapsules in cells.

To further confirm intracellular enzyme nanocapsule activity SOD nanocapsules were delivered in cells treated with paraquat, a intracellular superoxide generating compound. Superoxide ions, the by-products formed during an oxygen metabolism in aerobic cells, are implicated in the initiation and progression of a wide range of human diseases, such as inflammation, diabetes, carcinogenesis, ischemia/reperfusion injury and neurodegenerative diseases (Fridovich et al., *Ann. Rev. Pharmacol. Toxicol.*, vol. 23, pp. 239-257, 1983; Finkel et al., *Nature*, vol. 408, pp. 239-244, 2000; Ames et al., *Proc. Natl. Acad. Sci. USA*, vol. 90, pp. 7915-7922, 1993). SOD can effectively dismutate the superoxide anions and plays a key role in detoxifying free radicals and protects the cells from oxidative damage (McCord, J. M., *Method in Enzymol.*, vol. 349, pp. 331-341, 2002). Thus, the activity of intracellular SOD can be directly correlated to cell viability. FIG. 21B shows the relative cell viability after 2-hr incubation with the SOD nanocapsules followed by an exposure to 5 mM of paraquat for 12 hrs. The SOD nanocapsules effectively prevented the cells from oxidative injury at low nanocapsule concentrations. Increasing the nanocapsule concentration, however, lowers the cell viability. This curve is in accordance with the dose-response curves observed in a number of different myocardial ischemia-reperfusion models, which may be due to the production of increasing amount of hydroxyl radicals at high SOD concentration (Fridovich, I., *Ann. Rev. Pharmacol. Toxicol.*, vol. 23, pp. 239-57, 1983). Nonetheless, this work further proves the potential use of functional nanocapsules for various therapies or anti-aging agents.

Example 5

In Vivo Biodistribution

All animal experiments were performed in compliance with the Guidelines for the Care and Use of Research Animals established by the University of California at Los Angeles Chancellor's Animal Research Committee (ARC). Nude mice, 6-8 weeks old, were injected with 100 uL nanocapsule saline solution or saline solution (control). After 24 and 48 hrs, the mice were sacrificed and all major organs were extracted for ex vivo imaging. Then frozen organs containing the nanocapsules were embedded in a freezing medium and microtome in cryostat. The tissue sections containing the HRP nanocapsules were stained with dihydroethidium (Invitrogen) and observed using a confocal microscope.

Figure 22:
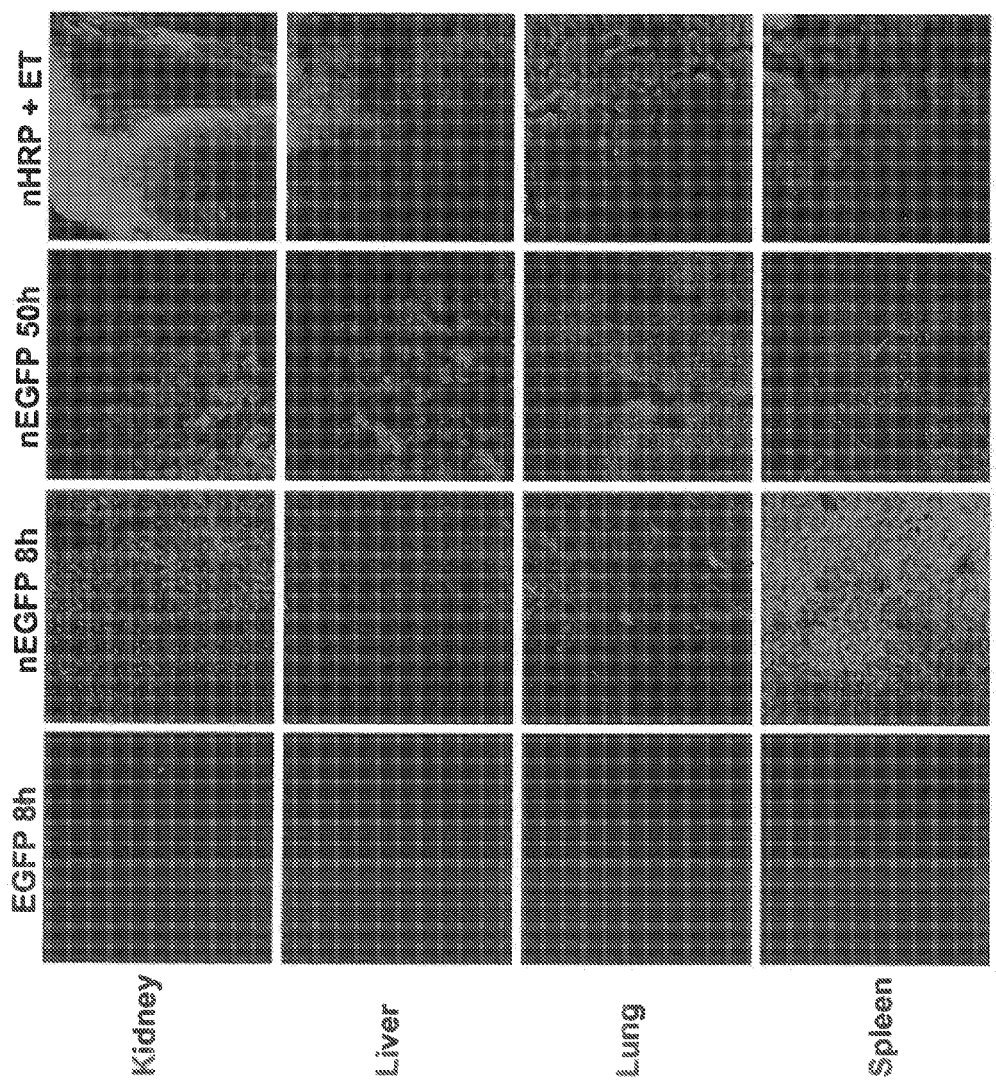
FIG. 22 shows confocal images of the tissue sections of C57BL/6 mice after administration of EGFP nanocapsules or HRP nanocapsules and exposure to 1 mM dihydroethidium.

In-vivo delivery of the nanocapsules was conducted by injecting nude mice intraperitoneally with 0.2 mg of the EGFP nanocapsules or with control EGFP. After 8 hrs, fluorescence confocal microscopy analysis of various organ sections revealed a strong signal in all tissues examined from nanocapsule-injected mice, whereas the signal in control EGFP-injected mice remained at background levels (FIG. 22). The fluorescence intensity decreases with time but still remains high even after 50 hrs of the injection. Such highly stable nanocapsules can be used as in vivo cell imaging markers that required long-term stability, such as stem cell imaging and tumor tracking. Furthermore, the injected Nanocapsules still remained active inside the tissue. For example, 8 hrs after injection of HRP nanocapsules or native HRP, mice were sacrificed, sectioned and the tissues were examined for HRP activity with dihydroethidium (a fluorescence substrate of HRP). From the fluorescence confocal microscope images, red fluorescence from the product ethidium was clearly observed, indicating the nanocapsules are active in vivo.

Example 6

Degradable Crosslinker-Containing Nanocapsules

Stability and pH-Induced Degradation

Figure 23:
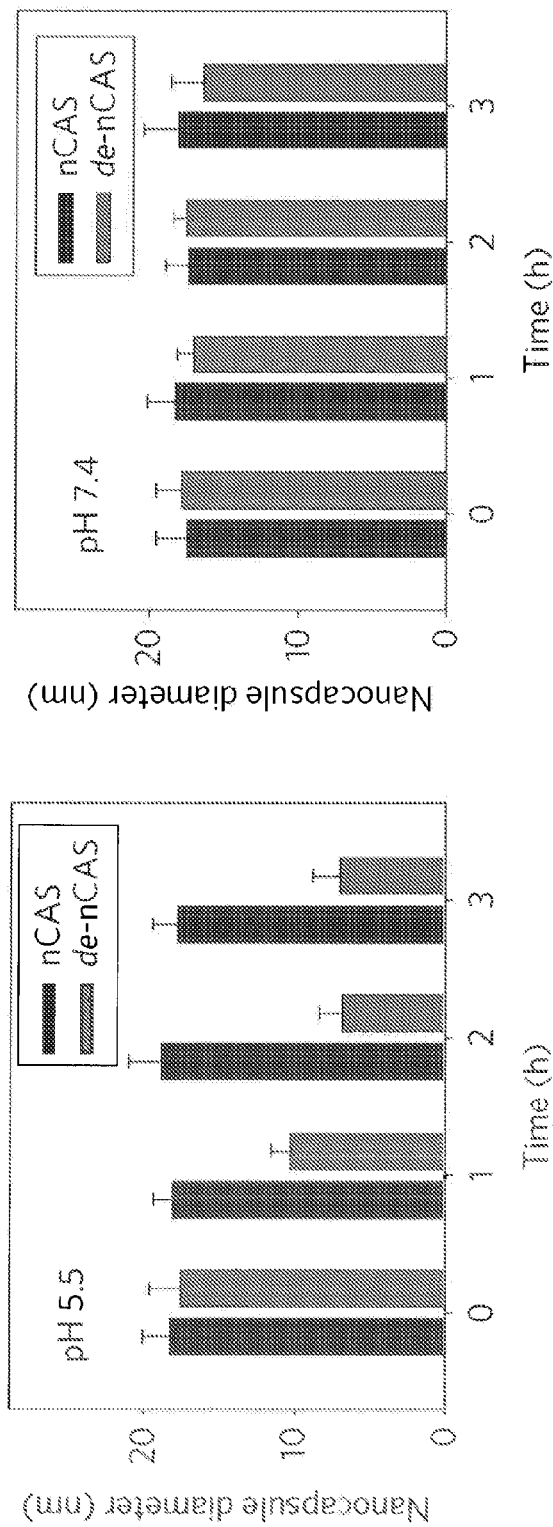
FIG. 23 shows size changes at different pH for exemplary degradable nanocapsules.
Figure 24:
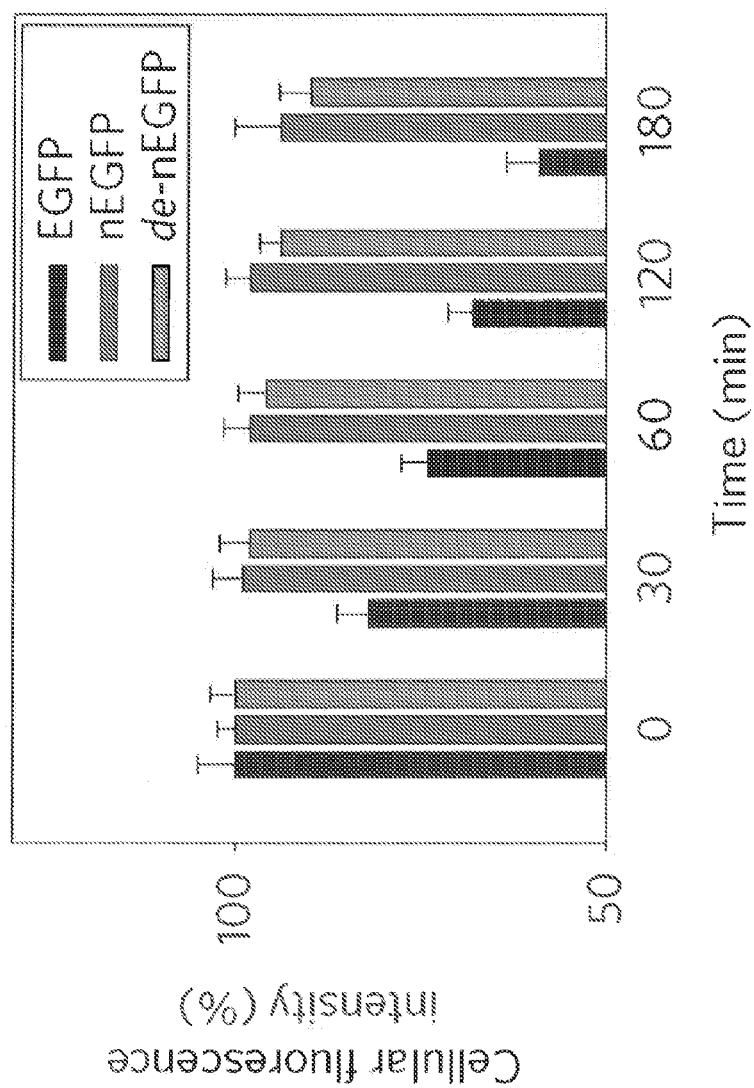
FIG. 24 shows fluorescence intensity of native EGFP, non-degradable EGFP nanocapsules (nEGFP) and degradable EGFP nanocapsules (de-nEGFP) after exposure to 1 mg ml$^{-1}$ trypsin and a-chymostrypsin in pH 7.4 buffer at 50° C. Fluorescence intensities are normalized to native EGFP before addition of proteases.

Using the non-degradable nanocapsule platform, it has been demonstrated that proteins for small molecule substrates can be effectively delivered with long-term stability and high activity. For macromolecular substrates, however, the polymer skin may prohibit their access to the core protein. It is well known that serum and late endosomes have pH values of ~7.4 and ~5.5, respectively. Acid degradable nanocapsules were therefore developed to overcome this obstacle. Using de-nCAS and nCAS as examples, the size evolution at pH 5.5 (FIG. 23A) and 7.4 (FIG. 23B) was studied. nCAS is stable at both values of pHs, but de-nCAS is only stable at pH 7.4. At pH 5.5, the average diameter of de-nCAS rapidly decreases within 3 h from 20 to 6 nm, a size similar to that of native CAS (~6 nm). Importantly, the degradable nanocapsules are stable against trypsin and a-chymotrypsin at pH 7.4 (FIG. 24), which allows the degradable nanocapsules to remain stable in the circulation system, to be degraded when inside endosomes to release their protein cargoes intracellularly.

Figure 25:
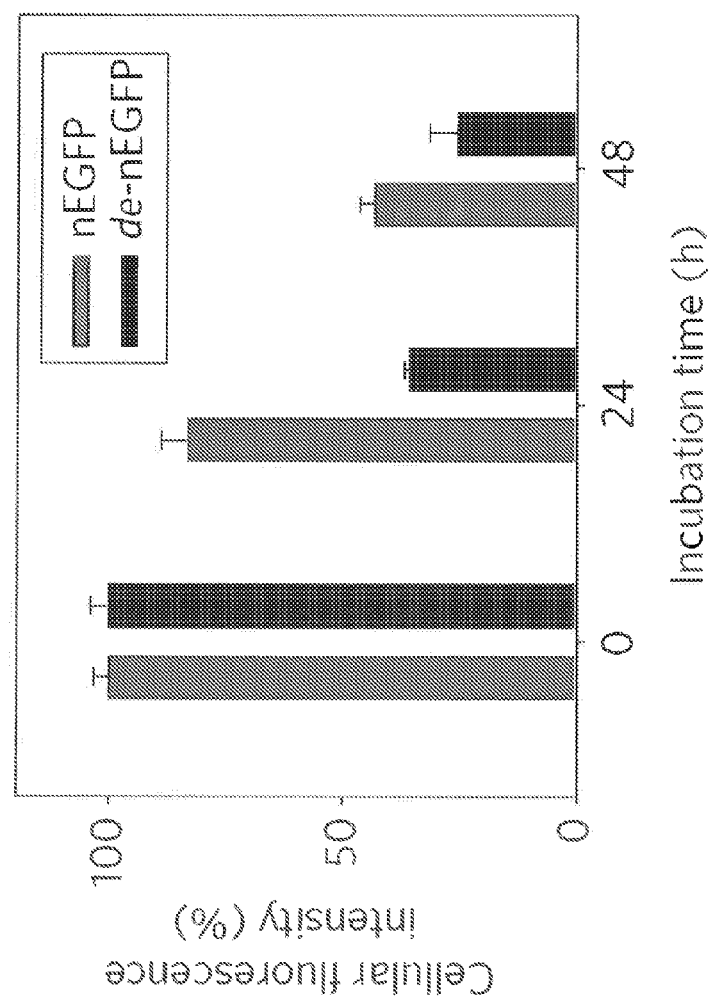
FIG. 25 shows fluorescence intensity of HeLa cells at different times after incubation with nEGFP or de-nEGFP for 3 h followed by incubation in fresh media. Fluorescence intensities are normalized to the respective cells that received no further incubation with fresh media.

To further quantify the intracellular degradation, de-nEGFP and nEGFP were delivered to HeLa cells. The cellular fluorescence intensities of the cells with de-nEGFP are significantly lower than those with nEGFP after 24 h (FIG. 25), confirming that degradable nanocapsules can be stripped of their shells in response to the acidic intercellular environment.

Apoptosis Inducement

Figure 26:
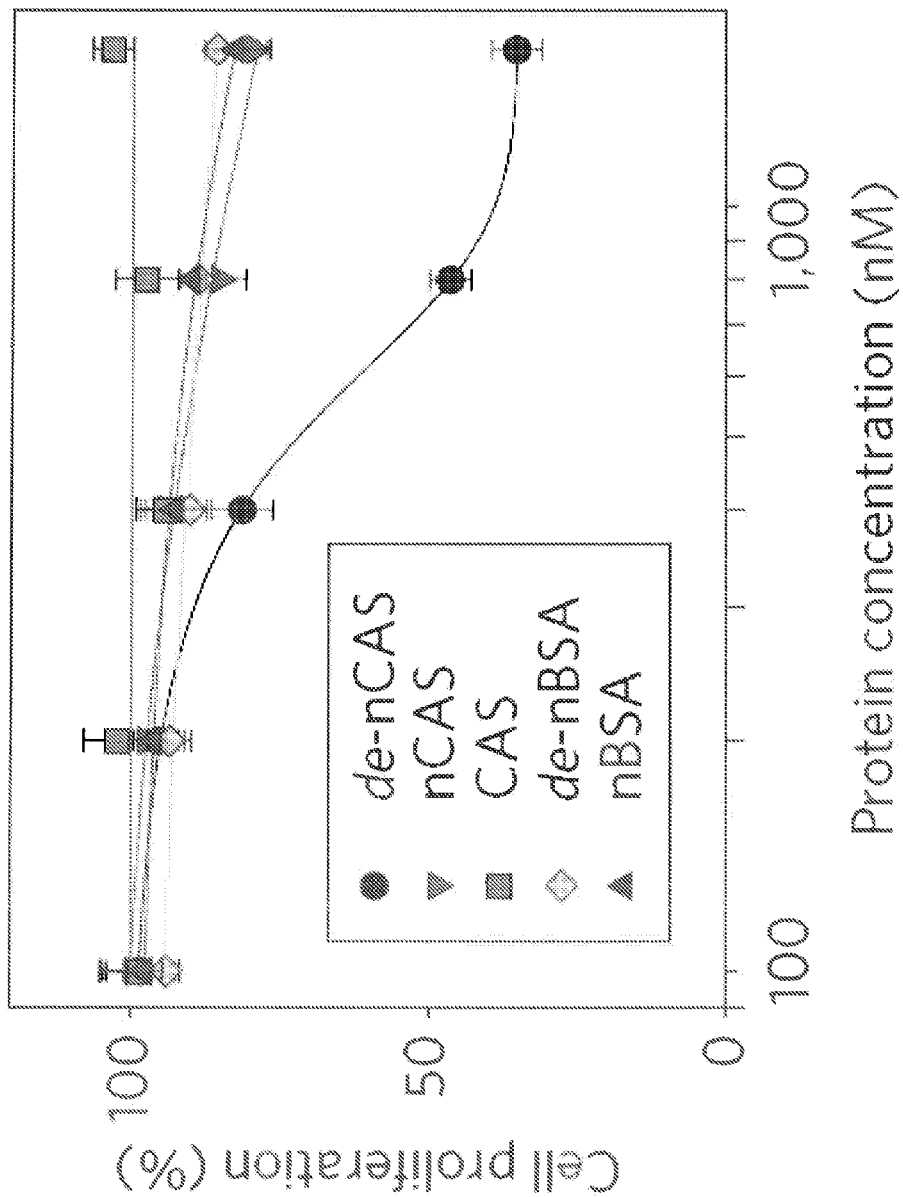
FIG. 26 shows MTT assay showing the cell proliferation profile after incubation with various concentrations of de-nCAS, nCAS, CAS, de-nBSA or nBSA for 48 h. Data are normalized to untreated cells.
Figure 27:
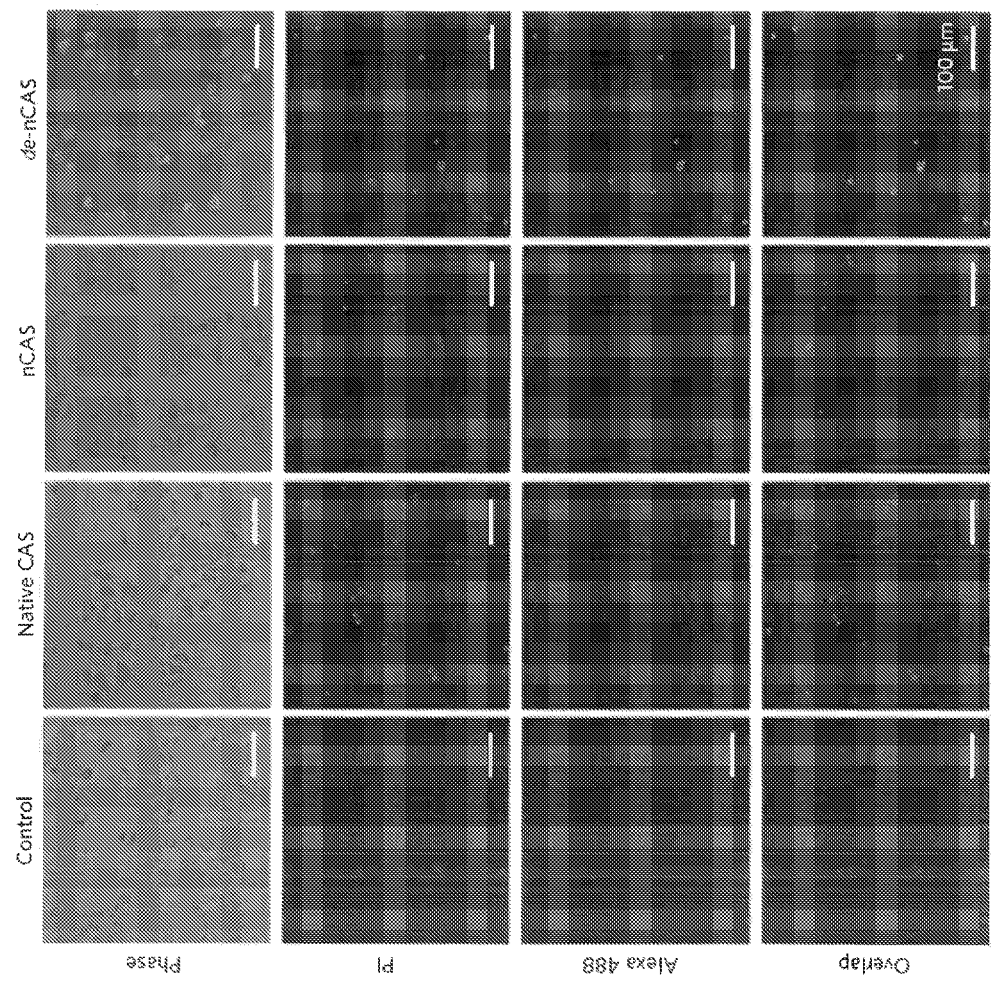
FIG. 27 shows APO-BrdUTM TUNEL assay showing HeLa cells transducted with native CAS, nCAS or de-nCAS. PI-stained nuclei and Alexa Fluor 488-stained nick end label in cells incubated with de-nCAS show apoptotic DNA fragmentation. Data represent averages, with error bars from three independent experiments performed in triplicate.

Although a de-protection process inevitably exposes the cargo proteins to protease attack, it enables their interaction with large substrates. For example, CAS, a member of the cysteine protease family that plays an essential role in apoptosis, necrosis and inflammation, cleaves other protein substrates within the cells to trigger apoptosis (Nicholson et al. Nature, vol. 376, pp. 37-43, 1995; Porter et al., Cell Death Differ., vol. 6, pp. 99-104, 1999; Oliver et al., Drug Resist. Updates, vol. 8, pp. 163-170, 2005). As shown in FIG. 26, incubation of HeLa cells with native CAS, nCAS, de-nBSA or nBSA demonstrates similar viabilities that are significantly higher than those with de-nCAS. Terminal dUTP nick-end labelling (TUNEL) assay (FIG. 27) confirms the apoptosis triggered by de-nCAS.

CONCLUSION

Intracellular use of fluorescence, illuminence and therapeutic proteins is of great importance for diagnosis and treatments of cancers and protein-deficient diseases. In 2007, the market for therapeutic proteins grew by almost 19% to $48 billion, and is predicted to achieve sales of over $90 billion by 2010. Future growth however depends largely on the industry overcoming a number of hurdles, including drug delivery challenges and cost issues. The therapeutic proteins such as angiotensin converting enzyme for hypertension, erythropoietin for anemia, interferon for hepatitis, glucocerebrosidase for Gaucher's disease and asparaginase for enzyme prodrug chemotherapy are recognized as specific and effective therapeutic drugs. The fluorescence and bioilluminence proteins such green-fluorescence protein, red-fluorescence protein and organic fluorescence molecule labeled protein, luciferases from firefly or beetles and horseradish peroxidase, are widely used in tumor and vascular imaging. These single protein polymer nanocapsules exhibit higher efficiency, activity, and stability in intracellular delivery both in vitro and in vivo than direct usage of natural proteins.

Protein imaging and therapy offers the most direct and safe approach for the diagnosis and treatment of cancers and protein-malfunctioned diseases. However, broad use of the protein imaging and therapy is still limited by several substantial technical barriers, such as low efficiency of intracellular delivery and poor stability of protein against proteases. These single protein polymer nanocapsules present a highly promising route for therapeutic, imaging and other applications for high efficiency, activity, and stability in intracellular delivery both in vitro and in vivo. They provide a better contrast and accuracy for protein-based imaging for cancer and a longer half-life, higher activity and lower dosages for protein therapy that those based on natural proteins.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

We claim:

1. A single-protein nanocapsule comprising a single-protein core and an artificial membrane covalently anchored to and encapsulating said single-protein, said artificial membrane comprising:
   (a) a polymer network comprising repeated units of at least two different monomer units which independently are positively charged, negatively charged, or uncharged, and hydrophobic or hydrophilic, wherein:
   said polymer network is crosslinked by a crosslinker comprising two or more polymerizable groups capable of forming a crosslinked co-polymer between the single protein core and at least one monomer unit; and
   said crosslinker is selected from the group consisting of N,N'-bis(acryloyl)cystamine, bis[2-(methacryloyloxy) ethyl]phosphate, and bisacryloylated polypeptide, and is disposed in the nanocapsule so as to be degradable in vivo;
   (b) a surface charge at physiological pH which is positive charge, negative charge or no charge; and
   (c) a modifiable moiety, wherein said single protein is more resistant to protease.

2. The single-protein capsule of claim 1, wherein said monomer unit is selected from the group consisting of: acrylamide, 2-hydroxyethyl acrylate, N-isopropylacrylamide, sodium acrylate, 2-acryloylamido-2-methylpropanesulfonic sodium, allyl amine, N-(3-aminopropyl) methacrylamide hydrochloride, dimethylamino ethyl methacrylate, (3-acrylamidopropyl)trimethylammonium hydrochloride, methyl acrylate, and styrene.

3. The single-protein capsule of claim 1, wherein said polymerizable group is selected from the group consisting of a vinyl group, an acryl group, and an alkylacryl group.

4. The single-protein capsule of claim 1, wherein said artificial membrane is covalently anchored to said single-protein core at at least 3 locations on said single protein.

5. The single-protein capsule of claim 4, wherein said locations are any of lysine, cysteine, threonine, glutamic acid, aspartic acid, serine, histidine, arginine, tyrosine, proline, and tryptophan.

6. The single-protein capsule of claim 1, wherein said modifiable moiety comprises a reactive group modified by a surface modifying agent.

7. The single-protein capsule of claim 6, wherein said surface modifying agent is selected from the group consisting of a small molecule, a polymer, a peptide, a polypeptide, a protein, an oligonucleotide, a polysaccharide, and an antibody.

8. The single-protein capsule of claim 6, wherein said surface modifying agent is an agent that alters solubility of said single-protein capsule, emits light, or effects cell targeting, or cell penetration.

9. The single-protein capsule of claim 1 which is transducible into a cell.

10. A plurality of single-protein nanocapsules according to claim 1, wherein the single proteins in said single-protein nanocapsules are same or different from each other.

11. A composition comprising a single-protein nanocapsule of claim 1 and a pharmaceutically acceptable carrier.

12. A composition comprising a plurality of single-protein nanocapsules according to claim 10 and a pharmaceutically acceptable carrier.

13. The single-protein capsule of claim 1, wherein said surface feature is a charge or solubility of the nanocapsule.

14. A single-protein nanocapsule comprising a single-protein core and an artificial membrane covalently anchored to and encapsulating said single-protein, said artificial membrane comprising a polymer network comprising repeated units of at least two different monomer units which independently are positively charged, negatively charged, or uncharged, and hydrophobic or hydrophilic, wherein:

said polymer network is crosslinked by a bis[2-(methacryloyloxy)ethyl]phosphate crosslinker comprising two or more polymerizable groups capable of forming a crosslinked co-polymer between the single protein core and at least one monomer unit; and said bis[2-(methacryloyloxy)ethyl]phosphate crosslinker is disposed in the nanocapsule so that the crosslinker:
(a) does not degrade at a first physiological pH; and
(b) degrades at a second physiological pH.

* * * * *